US007482455B2

(12) United States Patent
Burgess et al.

(10) Patent No.: US 7,482,455 B2
(45) Date of Patent: Jan. 27, 2009

(54) CHEMICAL COMPOUNDS

(75) Inventors: Joelle L. Burgess, King of Prussia, PA (US); James F. Callahan, King of Prussia, PA (US); Toshihiro Hamajima, Ibaraki (JP); Satoru Ida, Keita, NE (US); Ichiro Mori, Aichi (JP); Jun Tang, Ibaraki (JP)

(73) Assignee: SmithKline Beecham Corporation, Philadelphia, PA (US)

( * ) Notice: Subject to any disclaimer, the term of this patent is extended or adjusted under 35 U.S.C. 154(b) by 576 days.

(21) Appl. No.: 10/530,986

(22) PCT Filed: Oct. 15, 2003

(86) PCT No.: PCT/US03/32625

§ 371 (c)(1),
(2), (4) Date: Apr. 12, 2005

(87) PCT Pub. No.: WO2004/034985

PCT Pub. Date: Apr. 29, 2004

(65) Prior Publication Data

US 2006/0106058 A1    May 18, 2006

Related U.S. Application Data

(60) Provisional application No. 60/418,915, filed on Oct. 16, 2002.

(51) Int. Cl.
C07D 215/38 (2006.01)
(52) U.S. Cl. .................. 546/157; 546/156; 546/153
(58) Field of Classification Search .............. 546/153, 546/156, 157
See application file for complete search history.

(56) References Cited

U.S. PATENT DOCUMENTS

| 3,974,161 | A | * | 8/1976 | Althuis et al. .......... 544/250 |
| 4,044,134 | A | | 8/1977 | Althuis et al. |
| 5,441,949 | A | | 8/1995 | Jung et al. |
| 7,087,758 | B2 | * | 8/2006 | Bryan et al. .......... 546/161 |

FOREIGN PATENT DOCUMENTS

| DE | 2418498 | * | 11/1974 |
| DE | 2525050 | * | 1/1976 |
| EP | 0 581 500 | | 2/1994 |
| GB | 1465353 | * | 2/1977 |
| NL | 7603293 | * | 10/1976 |
| WO | 02/081728 | | 10/2002 |

OTHER PUBLICATIONS

El-Sayed, Archiv der Pharmazie, vol. 335(9), pp. 403-410, 2002.*
Boschelli, Bioorganic & Med Chem Lett, vol. 13(18), pp. 2977-2980, 2003.*
Althuis, J of Med chem, vol. 23(3), pp. 262-269, 1980.*
El-Sayed, abstract only CA 121:83189, abstract of Alexandria J of Pharm Sciences, vol. 7(2), pp. 163-166, 1993.*
Nakanishi, abstract only CA 93:204581, abstract of Org Prep and Proced Intern, vol. 12(3-4), pp. 219-223, 19870.*
Ouyang, et al., "Synthesis of 7, 8-methylenedioxy-4-oxo-3,4-dihydropyrimido [4,5-b]quinoline derivatives," Youji Huaxue, 15(1), 1995, pp. 99-103.
Chen, et al. "Synthesis of 3,4-dihydro-4-oxopyrimido[4,5-b]quinolines," Gadeng Xuexiao Huaxue Xuebao, 11(5), 1990, pp. 532-533.
Althuis et al., "Structure-activity relationships in a series of novel 3,4-dihydro-4-oxopyrimido[4,5-b]quinoline-2-carboxylic acid antiallergy agents," Journal of Medicinal Chemistry, 23(3), 1980, pp. 262-269.
Somasekhara, et al., "Sysnthesis of fused heterocyclics," Journal of the Indian Institute of Science, 37A, 1955, pp. 120-129.
Ganapathi, K., "Chemotherapy of baterial infections. II. Sythesis of some sulfanilamide derivatives and the relation of chemical constitution to chemotherapeutic action," Proceedings—Indian Academy of Sciences: Section A, 1940, 11A, pp. 298-311.
Troger et al., "Quinoline syntheses carried out with 6-amino-3-methoxybenzaldehyde and a condensation product resulting from this aldehyde," Journal Fuer Praktische Chemie, 1927, 117, pp. 97-116.
El-Syed, et al., "Synthesis of some novel quinoline-3-carboxylic acids and pyrimidoquinoline derivatives as potential antimicrobial agents," Archiv Der Pharamzie, 2002, 335(9), pp. 403-410.

* cited by examiner

Primary Examiner—D. Margaret Seaman
(74) Attorney, Agent, or Firm—John L. Lemanowicz

(57) ABSTRACT

3-carboxy quinoline derivatives, which are useful as YAK3 inhibitors are described herein. The described invention also includes methods of making such 3-carboxy quinoline derivatives as well as methods of using the same in the treatment of diseases mediated by inappropriate YAK3 activity.

4 Claims, No Drawings

CHEMICAL COMPOUNDS

This application is filed pursuant to 35 U.S.C. § 371 as a United States National Phase Application of International Application No. PCT/US2003/032625 filed Oct. 15, 2003, which claims priority from U.S. Ser. No. 60/418,915 filed Oct. 16, 2002.

BACKGROUND OF THE INVENTION

The present invention relates to 3-carboxy quinoline derivatives, compositions and medicaments containing the same, as well as processes for the preparation and use of such compounds, compositions and medicaments. Such 3-carboxy quinoline derivatives are useful in the treatment of diseases associated with inappropriate YAK3 activity.

The YAK family of serine/threonine protein kinases, represent a novel family of dual specificity protein kinases with unique structural, enzymatic, and probably functional features (Becker and Joost (1999) *Prog. Nucl. Acid Res.* 62, 1-17). Four members of the YAK family have been identified by large scale screening of human cDNA libraries using a yeast YAK1 sequence, and have been termed h (human)Yak1, 2, 3, and 4. (See U.S. Pat. No. 5,972,606 (hYAK1), U.S. Pat. No. 6,001,623 (hYAK2), and U.S. Pat. No. 5,965,420 (hYAK3)) In the yeast *S. cerevisiae* YAK1 functions as a negative regulator of cell growth (Garrett, S., Menold, M. M., and Broach, J. (1991) *Mol. Cell Biol.* 11, 4045-4051). Deletion of the three PKA genes (tpk1, tpk2, and tpk3) in yeast causes cell cycle arrest at $G_1$ while this growth defect is alleviated by removal of the YAK1 gene (Garrett, S., and Broach, J. (1989) *Gene Dev.* 3, 1336-1348). Recent data indicates that yYAK1 expression is controlled by two transcription factors MSN2/4 which are negatively regulated by PKA, thus yYAK1 acts downstream of PKA (Smith, A., Ward, M. P. and Garrett, S. (1998) EMBO J. 17, 3556-3564). While the means by which yYAK1 inhibits cell growth is still not known, overexpression of yYAK1 suppresses cell cycle arrest in late mitotic mutants (cdc15, cdc5, dbf2, and tem1) defective in anaphase-promoting complex (APC) (Jaspersen, S. L Charles, J. F., Tinker-Kulberg, R. L., and Morgan, D. O. (1998) *Mol. Biol. of the Cell.* 9, 2803-2817). Recent work in Dictyostelium has uncovered a yYAK1 homolog which is required for the transition from growth to development giving support to the involvement of this family of kinases in cell growth (Souza, G. M., Lu, S. and Kuspa, A. (1998) Development 125, Northern analysis was carried out to determine the distribution of hYAK3 mRNA in human tissues. Membranes containing mRNA from multiple human tissues (Clontech #7760-1, #7759-1, and #7768-1) were hybridized to an hYAK3 probe and washed under high stringency conditions as directed. Hybridized mRNA was visualized by exposing the membranes to X-ray film. One major transcript at ~2.5 kb was present in testis, and transcripts of 2.5, 8 and 10 kb were present in bone and fetal liver. The transcripts were not visible in any other tissues; however, dot blot analysis using a Human Master blot (Clontech #7770-1) indicated that hYAK3 is expressed in other tissues including skeletal muscle.

Investigations with primary cells and hematopoietic cell lines from both human and mouse indicate that cells of the erythroid lineage may predominantly account for the elevated hYAK3 expression. These data suggest that hYAK3 may have a lineage-specific function. In cell lines, hYAK3 is present at higher levels in cells with an erythroid phenotype than other hematopoietic lineages, including myeloid, monocytic and lymphoid cell lines. This profile is completely distinct from hYAK1, which has been observed only at low constitutive levels in hematopoietic cells and tissues. EPO-treatment of human bone marrow in vitro leads to induction and sustained expression of hYAK3 message and hYAK3 protein. Splenocytes from mice made anemic by phenylhydrazine treatment become enriched in erythroid progenitors and exhibit increased expression of hYAK3. Increases in both message and protein accompany induction of erythroid differentiation in UT7-EPO cells.

In yeast, yYAK is a negative regulator of growth via the cell cycle. Consequently, we would anticipate that hYAK3 participates in cell cycle control, and/or commitment to differentiation. We predict that an antagonist of hYAK3 would have a positive effect on cell growth. Our data indicates that it also may be involved in terminal differentiation and growth arrest in hematopoietic cells, especially in the erythroid lineage.

The present inventors have discovered novel 3-carboxy quinoline compounds, which are inhibitors of YAK3 activity. Such 3-carboxy quinoline derivatives are useful in the treatment of disorders associated with inappropriate YAK3 activity, especially diseases of the hematopoietic systems, including anemias due to renal insufficiency or to chronic disease, such as autoimmunity or cancer and drug-induced anemias, polycythemia, myelodysplastic syndrome, aplastic anemia and myelosuppression; cytopenia; neurodegeneration; and also for controlling male fertility, especially for the purpose of achieving contraception.

BRIEF SUMMARY OF THE INVENTION

In one aspect of the present invention, there is provided a compound of Formula (I):

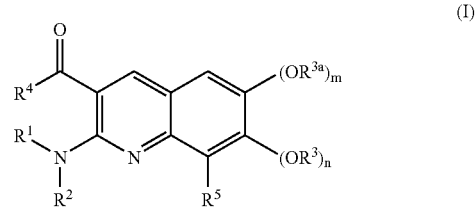

wherein:
 $R^1$ is —H or $C_1$-$C_6$ alkyl;
 $R^2$ is the group defined by -$(Q)_q$-$(Q^1)_r$-$(Q^2)$, wherein:
 Q is $CH_2$ and q is 0, 1, 2, 3, or 4;
 $Q^1$ is O, NH, or C(H)(R') where R' is —OH; and r is 0 or 1, and
 $Q^2$ is —H, $C_1$-$C_6$ alkyl, aryl, heterocyclic, $C_3$-$C_7$ cycloalkyl, —C(O)$OR^b$, $NR^bR^b$, or heteroaryl; where $Q^2$ is optionally substituted with at least one $R^a$ group;
 $R^3$ and $R^{3a}$ are independently selected from —H, $C_1$-$C_6$ alkyl, or $C_1$-$C_6$ hydroxyalkyl, m is 0 or 1, and n is 0 or 1, or
 m is 1 and n is 1 and $R^3$ and $R^{3a}$ together with the atoms to which they are attached form the optionally substituted fused ring

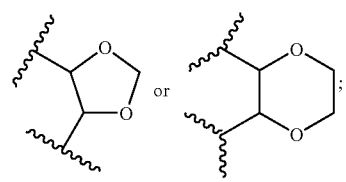

$R^4$ is —OH, —NHS(O)$_2R^c$, or —N($R^b$)R;
 $R^5$ is —H or halo;
 $R^6$ is —H, aryl, —$OR^b$;

$R^a$ is independently selected from $C_1$-$C_6$ alkyl, halo, aryl, —C(O)O$R^b$, —C(O)$R^d$, —OH, —N$R^b R^b$, —N(H)C(O)O$R^b$, —N(H)C(O)N(H)$R^e$, —N(H)S(O)$_2 R^e$, —N(H)S(O)$_2$N$R^b R^b$, $C_1$-$C_6$ alkoxy, $C_1$-$C_6$ haloalkyl, —NO$_2$, —CN, —SF$_5$, =O, —S(O)$_2$N$R^b R^b$, or aryloxy;

$R^b$ is —H, $C_1$-$C_6$ alkyl, or $C_2$-$C_4$ alkenyl;

$R^c$ is aryl or $C_1$-$C_6$ alkyl;

$R^d$ is $C_1$-$C_6$ alkyl, aryl, N$R^b R^b$, or N(H)(CH$_2$)$_s$N$R^b R^b$, $R^e$ is —H, aryl or $C_1$-$C_6$ alkyl;

s is 1, 2, 3, or 4;

or a pharmaceutically acceptable salt or solvate thereof.

In a second aspect of the present invention, there is provided a pharmaceutical composition comprising a therapeutically effective amount of a compound of formula (I) or a salt, solvate, or a physiologically functional derivative thereof and one or more of pharmaceutically acceptable carriers, diluents and excipients.

In a third aspect of the present invention, there is provided a method of treating a disorder in a mammal, said disorder being mediated by inappropriate YAK3 activity, comprising: administering to said mammal a therapeutically effective amount of a compound of formula (I) or a salt, solvate or a physiologically functional derivative thereof.

In a fourth aspect of the present invention, there is provided a compound of formula (I), or a salt, solvate, or a physiologically functional derivative thereof for use in therapy.

In a fifth aspect of the present invention, there is provided the use of a compound of formula (I), or a salt, solvate, or a physiologically functional derivative thereof in the preparation of a medicament for use in the treatment of a disorder mediated by inappropriate YAK3 activity.

DETAILED DESCRIPTION

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein the term "alkyl" refers to a straight- or branched-chain hydrocarbon radical having from one to twelve carbon atoms, optionally substituted with substituents selected from the group consisting of $C_1$-$C_6$ alkyl, $C_1$-$C_6$ hydroxyalkyl, $C_1$-$C_6$ alkoxy, $C_1$-$C_6$ alkylsulfanyl, $C_1$-$C_6$ alkylsulfenyl, $C_1$-$C_6$ alkylsulfonyl, oxo, hydroxy, mercapto, amino optionally substituted by alkyl, carboxy, carbamoyl optionally substituted by alkyl, aryl, aryloxy, heteroaryl, aminosulfonyl optionally substituted by alkyl, nitro, cyano, halo, or $C_1$-$C_6$ perfluoroalkyl, multiple degrees of substitution being allowed. Examples of "alkyl" as used herein include, but are not limited to, methyl, ethyl, n-propyl, isopropyl, n-butyl, isobutyl, t-butyl, n-pentyl, isopentyl, and the like.

As used herein, the term "$C_1$-$C_6$ alkyl" refers to an alkyl group, as defined above, containing at least 1, and at most 6 carbon atoms. Examples of such branched or straight-chained alkyl groups useful in the present invention include, but are not limited to, methyl, ethyl, n-propyl, isopropyl, isobutyl, n-butyl, t-butyl, n-pentyl, isopentyl, and n-hexyl.

As used herein, the term "alkylene" refers to a straight or branched chain divalent hydrocarbon radical having from one to ten carbon atoms, optionally substituted with substituents selected from the group which includes $C_1$-$C_6$ alkyl, $C_1$-$C_6$ alkoxy, $C_1$-$C_6$ alkylsulfanyl, $C_1$-$C_6$ alkylsulfenyl, $C_1$-$C_6$ alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halo, and $C_1$-$C_6$ perfluoroalkyl, multiple degrees of substitution being allowed. Examples of "alkylene" as used herein include, but are not limited to, methylene, ethylene, n-propylene, n-butylene, and the like.

As used herein, the terms "$C_1$-$C_3$ alkylene" and "$C_1$-$C_6$ alkylene" refer to an alkylene group, as defined above, which contains at least 1, and at most 3 or 6, carbon atoms respectively. Examples of "$C_1$-$C_3$ alkylene" and "$C_1$-$C_6$ alkylene" groups useful in the present invention include, but are not limited to, methylene, ethylene, n-propylene, n-butylene, isopentylene, and the like.

As used herein, the term "halogen" refers to fluorine (F), chlorine (Cl), bromine (Br), or iodine (I) and the term "halo" refers to the halogen radicals: fluoro (—F), chloro (—Cl), bromo(—Br), and iodo(—I).

As used herein, the term "$C_1$-$C_6$ haloalkyl" refers to an alkyl group as defined above containing at least 1, and at most 6 carbon atoms substituted with at least one halo group, halo being as defined herein. Examples of such branched or straight chained haloalkyl groups useful in the present invention include, but are not limited to, methyl, ethyl, propyl, isopropyl, isobutyl and n-butyl substituted independently with one or more halos, e.g., fluoro, chloro, bromo and iodo.

As used herein, the term "$C_1$-$C_6$ hydroxyalkyl" refers to an alkyl group as defined above containing at least 1, and at most 6 carbon atoms substituted with at least one hydroxy group, hydroxy being as defined herein. Examples of such branched or straight chained hydroxyalkyl groups useful in the present invention include, but are not limited to, methyl, ethyl, propyl, isopropyl, isobutyl and n-butyl substituted with one or more hydroxy groups.

As used herein, the term "cycloalkyl" refers to a non-aromatic cyclic hydrocarbon ring containing from 3 to 10 carbon atoms and which optionally includes a $C_1$-$C_6$ alkylene linker through which it may be attached. In a like manner the term "$C_3$-$C_7$ cycloalkyl" refers to a non-aromatic cyclic hydrocarbon ring having from three to seven carbon atoms and which optionally includes a $C_1$-$C_6$ alkylene linker through which it may be attached. The $C_1$-$C_6$ alkylene group is as defined above. Exemplary "$C_3$-$C_7$ cycloalkyl" groups useful in the present invention include, but are not limited to, cyclopropyl, cyclobutyl, cyclopentyl, cyclohexyl and cycloheptyl.

As used herein, the term "heterocyclic" or the term "heterocyclyl" refers to a three to twelve-membered non-aromatic heterocyclic ring, being saturated or having one or more degrees of unsaturation, containing one or more heteroatom substitutions selected from S, S(O), S(O)$_2$, O, or N, optionally substituted with substituents selected from the group consisting of $C_1$-$C_6$ alkyl, $C_1$-$C_6$ alkoxy, $C_1$-$C_6$ alkylsulfanyl, $C_1$-$C_6$ alkylsulfenyl, $C_1$-$C_6$ alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halo, aryl, aralkyl, heteroaryl, or $C_1$-$C_6$ perfluoroalkyl, multiple degrees of substitution being allowed. Such a ring may be optionally fused to one or more other "heterocyclic" ring(s), cycloalkyl ring(s), or aryl ring(s). Examples of "heterocyclic" moieties include, but are not limited to, tetrahydrofuranyl such as tetrahydrofuran-2-yl, pyranyl, 1,4-dioxanyl, 1,3-dioxanyl, piperidinyl such as piperdin-1-yl, piperazinyl such as 4-tert-butoxycarbonyl-piperazin-1-yl, 2,4-piperazinedionyl, pyrrolidinyl such as 2-oxo-pyrrolidin-1-yl and pyrrolidin-2-yl, imidazolidinyl such as 2-oxo-imidazolidin-1-yl, pyrazolidinyl, morpholinyl such as morpholin-4-yl, thiomorpholinyl, tetrahydrothiopyranyl, tetra hydrothiophenyl, benzodioxyl such as benzo [1,3]dioxol-5-yl, and the like as well as additional substituted versions thereof.

As used herein, the term "aryl" refers to an optionally substituted benzene ring or to an optionally substituted benzene ring system fused to one or more optionally substituted benzene or cycloalkyl rings to form, for example, anthracene, phenanthrene, indan, or napthalene ring systems. Exemplary optional substituents include $C_1$-$C_6$ alkyl, $C_1$-$C_6$ alkoxy, $C_1$-$C_6$ haloalkyl, $C_1$-$C_6$ haloalkoxy, $C_1$-$C_6$ alkylsulfanyl, $C_1$-$C_6$ alkylsulfenyl, $C_1$-$C_6$ alkylsulfonyl, $C_1$-$C_6$ alkylsulfonylamino, arylsulfonoamino, alkylcarboxy, alkylcarboxyamide, oxo, hydroxy, mercapto, amino optionally substituted by alkyl or acyl, carboxy, tetrazolyl, carbamoyl optionally substituted by alkyl, aryl, or heteroaryl, aminosulfonyl optionally substituted by alkyl, acyl, aroyl, aroylamino, heteroaroyl, acyloxy, aroyloxy, heteroaroyloxy, alkoxycarbonyl, nitro, cyano, halo, heteroaryl, heterocyclyl, aryl optionally substituted with aryl, halo, $C_1$-$C_6$ alkyl, $C_1$-$C_6$ haloalkyl, or $C_1$-$C_6$ alkylsulfonyl, ureido, arylurea, alkylurea, cycloalkylurea, alkylthiourea, aryloxy, or aralkoxy, multiple degrees of substitution being allowed. Examples of "aryl" groups include, but are not limited to, phenyl, 2-naphthyl, 1-naphthyl, biphenyl, indanyl, tetrahydronaphthylenyl, as well as substituted derivatives thereof.

As used herein, the term "aralkyl" refers to an aryl or heteroaryl group, as defined herein, attached through a $C_1$-$C_3$ alkylene linker, wherein the $C_1$-$C_3$ alkylene is as defined herein. Examples of "aralkyl" include, but are not limited to, benzyl, phenylpropyl, phenylethyl, 2-pyridylmethyl, 3-isoxazolylmethyl, 5-methyl-3-isoxazolylmethyl, and 2-imidazolyl ethyl.

As used herein, the term "heteroaryl" refers to a monocyclic five to seven membered aromatic ring, or to a fused bicyclic or tricyclic aromatic ring system comprising two of such monocyclic five to seven membered aromatic rings. These heteroaryl rings contain one or more nitrogen, sulfur, and/or oxygen heteroatoms, where N-oxides and sulfur oxides and dioxides are permissible heteroatom substitutions and may be optionally substituted with up to three members selected from a group consisting of $C_1$-$C_6$ alkyl, $C_1$-$C_6$ alkoxy, $C_1$-$C_6$ alkylsulfanyl, $C_1$-$C_6$ alkylsulfenyl, $C_1$-$C_6$ alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halo, $C_1$-$C_6$ perfluoroalkyl, heteroaryl, or aryl, multiple degrees of substitution being allowed. Examples of "heteroaryl" groups used herein include, but are not limited to, furanyl, thiophenyl, pyrrolyl, imidazolyl, pyrazolyl, triazolyl, tetrazolyl, thiazolyl, oxazolyl, isoxazolyl, oxadiazolyl, oxo-pyridyl, thiadiazolyl, isothiazolyl, pyridyl, pyridazyl, pyrazinyl, pyrimidyl, quinolinyl, isoquinolinyl, benzofuranyl, benzothiophenyl, indolyl, indazolyl, and substituted versions thereof.

As used herein, the term "alkoxy" refers to the group $R_aO$—, where $R_a$ is alkyl as defined above and the term "$C_1$-$C_6$ alkoxy" refers to an alkoxy group as defined herein wherein the alkyl moiety contains at least 1, and at most 6, carbon atoms. Exemplary $C_1$-$C_6$ alkoxy" groups useful in the present invention include, but are not limited to, methoxy, ethoxy, n-propoxy, isopropoxy, n-butoxy, and t-butoxy.

As used herein, the term "amino" refers to the group —$NH_2$.

As used herein the term "alkylamino" refers to the group —$NHR_a$ wherein $R_a$ is alkyl as defined above.

As used herein the term "arylamino" refers to the group —$NHR_a$ wherein $R_a$ is aryl as defined above.

As used herein the term "aralkylamino" refers to the group —$NHR_a$ wherein $R_a$ is an aralkyl group as defined above.

As used herein the term "aralkoxy" refers to the group $R_bR_aO$—, where $R_a$ is alkylene and $R_b$ is aryl or heteroaryl all as defined above.

As used herein the term "aryloxy" refers to the group $R_aO$—, where $R_a$ is aryl or heteroaryl both as defined above.

As used herein the term "ureido" refers to the group —$NHC(O)NH_2$

As used herein, the term "arylurea" refers to the group —$NHC(O)NHR_a$ wherein $R_a$ is aryl as defined above.

As used herein, the term "arylthiourea" refers to the group —$NHC(S)NHR_a$ wherein $R_a$ is aryl as defined above.

As used herein, the term "alkylurea" refers to the group —$NHC(O)NHR_a$ wherein $R_a$ is alkyl as defined above.

As used herein, the term "cycloalkylurea" refers to the group —$NHC(O)NHR_a$ wherein $R_a$ is cycloalkyl as defined above.

As used herein, the term "$C_3$-$C_7$ cycloalkoxy" refers to the group $R_aO$—, where $R_a$ is $C_3$-$C_7$ cycloalkyl as defined above. Exemplary $C_3$-$C_7$ cycloalkoxy groups useful in the present invention include, but are not limited to, cyclobutoxy, and cyclopentoxy.

As used herein, the term "haloalkoxy" refers to the group $R_aO$—, where $R_a$ is haloalkyl as defined above and the term "$C_1$-$C_6$ haloalkoxy" refers to a haloalkoxy group as defined herein wherein the haloalkyl moiety contains at least 1, and at most 6, carbon atoms. Exemplary $C_1$-$C_6$ haloalkoxy groups useful in the present invention include, but is not limited to, trifluoromethoxy.

As used herein, the term "alkylsulfanyl" refers to the group $R_aS$—, where $R_a$ is alkyl as defined above and the term "$C_1$-$C_6$ alkylsulfanyl" refers to an alkylsulfanyl group as defined herein wherein the alkyl moiety contains at least 1, and at most 6, carbon atoms.

As used herein, the term "haloalkylsulfanyl" refers to the group $R_aS$—, where $R_a$ is haloalkyl as defined above and the term "$C_1$-$C_6$ haloalkylsulfanyl" refers to a haloalkylsulfanyl group as defined herein wherein the alkyl moiety contains at least 1, and at most 6, carbon atoms.

As used herein, the term "alkylsulfenyl" refers to the group $R_aS(O)$—, where $R_a$ is alkyl as defined above and the term "$C_1$-$C_6$ alkylsulfenyl" refers to an alkylsulfenyl group as defined herein wherein the alkyl moiety contains at least 1, and at most 6, carbon atoms.

As used herein, the term "alkylsulfonyl" refers to the group $R_aS(O)_2$—, where $R_a$ is alkyl as defined above and the term "$C_1$-$C_6$ alkylsulfonyl" refers to an alkylsulfonyl group as defined herein wherein the alkyl moiety contains at least 1, and at most 6, carbon atoms.

As used herein, the term "alkylsulfonylamino" refers to the group —$NHS(O)_2R_a$ wherein $R_a$ is alkyl as defined above and the term "$C_1$-$C_6$ alkylsulfonylamino" refers to an alkylsulfonylamino group as defined herein wherein the alkyl moiety contains at least 1, and at most 6, carbon atoms.

As used herein, the term "arylsulfonylamino" refers to the group —$NHS(O)_2R_a$ wherein $R_a$ is aryl as defined above.

As used herein, the term "alkylcarboxyamide" refers to the group —$NHC(O)R_a$ wherein $R_a$ is alkyl, amino, or amino substituted with alkyl, aryl or heteroaryl as described above.

As used herein the term "alkylcarboxy" refers to the group —C(O)$R_a$ wherein $R_a$ is alkyl as described above.

As used herein the term "hydroxy" refers to the group —OH.

As used herein, the term "oxo" refers to the group =O.

As used herein, the term "mercapto" refers to the group —SH.

As used herein, the term "carboxy" refers to the group —C(O)O$R_a$, wherein $R_a$ is H or alkyl as defined herein.

As used herein, the term "cyano" refers to the group —CN.

As used herein the term "cyanoalkyl" refers to the group —$R_a$CN wherein $R_a$ is alkyl as defined above. Exemplary "cyanoalkyl" groups useful in the present invention include, but are not limited to, cyanomethyl, cyanoethyl, and cyanoisopropyl.

As used herein, the term "aminosulfonyl" refers to the group —S(O)$_2$NH$_2$.

As used herein, the term "carbamoyl" refers to the group —OC(O)NH$R_a$, where $R_a$ is hydrogen or alkyl as defined herein.

As used herein, the term "carboxamide" refers to the group —C(O)NH$_2$.

As used herein, the term "sulfanyl" shall refer to the group —S—.

As used herein, the term "sulfenyl" shall refer to the group —S(O)—.

As used herein, the term "sulfonyl" shall refer to the group —S(O)$_2$— or —SO$_2$—.

As used herein, the term "acyl" refers to the group $R_a$C(O)—, where $R_a$ is alkyl, cycloalkyl, or heterocyclyl as defined herein.

As used herein, the term "aroyl" refers to the group $R_a$C(O)—, where $R_a$ is aryl as defined herein.

As used herein, the term "aroylamino" refers to the group $R_a$C(O)NH—, where $R_a$ is aryl as defined herein.

As used herein, the term "heteroaroyl" refers to the group $R_a$C(O)—, where $R_a$ is heteroaryl as defined herein.

As used herein, the term "alkoxycarbonyl" refers to the group $R_a$OC(O)—, where $R_a$ is alkyl as defined herein.

As used herein, the term "acyloxy" refers to the group $R_a$C(O)O—, where $R_a$ is alkyl, cycloalkyl, or heterocyclyl as defined herein.

As used herein, the term "aroyloxy" refers to the group $R_a$C(O)O—, where $R_a$ is aryl as defined herein.

As used herein, the term "heteroaroyloxy" refers to the group $R_a$C(O)O—, where $R_a$ is heteroaryl as defined herein.

As used herein, the term "optionally" means that the subsequently described event(s) may or may not occur, and includes both event(s), which occur, and events that do not occur.

As used herein, the term "physiologically functional derivative" refers to any pharmaceutically acceptable derivative of a compound of the present invention, for example, an ester or an amide, which upon administration to a mammal is capable of providing (directly or indirectly) a compound of the present invention or an active metabolite thereof. Such derivatives are clear to those skilled in the art, without undue experimentation, and with reference to the teaching of Burger's Medicinal Chemistry And Drug Discovery, 5$^{th}$ Edition, Vol 1: Principles and Practice, which is incorporated herein by reference to the extent that it teaches physiologically functional derivatives.

As used herein, the term "solvate" refers to a complex of variable stoichiometry formed by a solute (in this invention, a compound of formula (I) or a salt or physiologically functional derivative thereof) and a solvent. Such solvents for the purpose of the invention may not interfere with the biological activity of the solute. Examples of suitable solvents include, but are not limited to, water, methanol, ethanol and acetic acid. Preferably the solvent used is a pharmaceutically acceptable solvent. Examples of suitable pharmaceutically acceptable solvents include, without limitation, water, ethanol and acetic acid. Most preferably the solvent used is water.

As used herein, the term "substituted" refers to substitution with the named substituent or substituents, multiple degrees of substitution being allowed unless otherwise stated.

Certain of the compounds described herein may contain one or more chiral atoms, or may otherwise be capable of existing as two enantiomers. The compounds of this invention include mixtures of enantiomers as well as purified enantiomers or enantiomerically enriched mixtures. Also included within the scope of the invention are the individual isomers of the compounds represented by formula (I) above as well as any wholly or partially equilibrated mixtures thereof. The present invention also covers the individual isomers of the compounds represented by the formulas above as mixtures with isomers thereof in which one or more chiral centers are inverted. Also, it is understood that any tautomers and mixtures of tautomers of the compounds of formula (I) are included within the scope of the compounds of formula (1).

It is understood that due to the presence of the double bond containing alkenylene chain in formula (I), also included within the scope of formula (I) are the respective pure E and Z geometric isomers as well as mixtures of E and Z isomers of the compounds of formula (I). The invention as described and claimed does not set any limiting ratios on prevalence of Z to E isomers.

In one embodiment, the compounds of formula (I) are in the form of a substantially pure E geometric isomer. In another embodiment, the compounds of formula (I) are in the form of a substantially pure Z geometric isomer. In a further embodiment, the compounds of formula (I) are in the form of a mixture of E geometric isomer and Z geometric isomer in any proportions of said geometric isomers.

It is to be understood that reference to compounds of formula (I) above, following herein, refers to compounds within the scope of formula (I) as defined above with respect to $R^1$, $R^2$, $R^3$, $R^{3a}$, $R^4$, $R^5$, R, $R^a$, $R^b$, $R^c$, $R^d$, $R^e$, q, r, s, Q, $Q^1$, and $Q^2$ unless specifically limited otherwise.

In one embodiment, $R^1$ is —H or methyl, preferably $R^1$ is —H.

As indicated above, $R^2$ is a group defined by -(Q)$_q$-($Q^1$)$_r$-($Q^2$). In one embodiment, q and r are 0, and $R^2$ is -($Q^2$). In another embodiment, q is 1, 2, 3, or 4, r is 0 and $R^2$ is -(Q)$_q$-($Q^2$). In another embodiment, q is 0, r is 1, and $R^2$ is -($Q^1$)-($Q^2$). In another embodiment, q is 1, 2, 3, or 4 and r are 1, and $R^2$ is -(Q)$_q$-($Q^1$)-($Q^2$).

In one embodiment, q is 1, 2, 3, or 4 and Q is CH$_2$. In another embodiment, q is 1, 2, or 3 and Q is CH$_2$. In a preferred embodiment, q is 1 or 2 and Q is CH$_2$.

In one embodiment, r is 0 or 1 and $Q^1$ is NH or O. In another embodiment, r is 0 or 1 and $Q^1$ is NH. In a preferred embodiment, r is 0.

In one embodiment, $Q^2$ is $C_1$-$C_6$ alkyl, aryl, heterocyclic, $C_3$-$C_7$cycloalkyl, or heteroaryl each optionally substituted with at least one $R^a$ group, wherein $R^a$ is as defined above. In another embodiment, $Q^2$ is aryl optionally substituted with at least one $R^a$ group, wherein $R^a$ is as defined above.

In one embodiment, $R^2$ is a group defined by -(Q)$_q$-($Q^1$)$_r$-($Q^2$), where Q is CH$^2$, q is 1, 2, 3, or 4, r is 0, and $Q^2$ is aryl optionally substituted with at least one $R^a$ group, wherein $R^a$ is as defined above, preferably Q is CH$^2$, q is 1, 2, or 3, r is 0, and $Q^2$ is phenyl optionally substituted with at least one $R^a$ group, wherein $R^a$ is as defined above, more preferably Q is CH², q is 2, r is 0, and Q² is phenyl optionally substituted with at least one Rᵃ group, wherein Rᵃ is as defined above.

In another embodiment, R² is a group defined by -(Q)$_q$-(Q¹)$_r$-(Q²), where q is 0, r is 0, and Q² is aryl optionally substituted with at least one Rᵃ group, wherein Rᵃ is as defined above, preferably q is 0, r is 0, and Q² is phenyl optionally substituted with at least one Rᵃ group, wherein Rᵃ is as defined above.

In another embodiment, R² is a group defined by -(Q)$_q$-(Q¹)$_r$-(Q²), where q is 0, r is 0, and Q² is C₁-C₆ alkyl optionally substituted with at least one Rᵃ group, wherein Rᵃ is as defined above.

In one embodiment, m is 0, n is 1, and R³ is —H or C₁-C₆ alkyl, preferably m is 0, n is 1, and R³ is —H or methyl. In an alternative embodiment, m is 1, n is 0, and R³ᵃ is —H or C₁-C₆ alkyl, preferably m is 1, n is 0, and R³ᵃ is —H or methyl.

In another embodiment, m is 1 and n is 1 and R³ and R³ᵃ together with the atoms to which they are attached form the optionally substituted fused ring

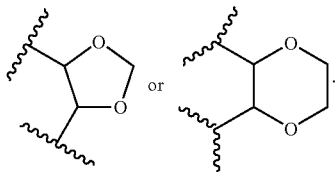

It will be understood by those skilled in the art that the range of optional substituents will vary according to, which R³ and R³ᵃ groups form the fuse ring.

In one embodiment, R⁴ is —NHS(O)₂Rᶜ, wherein Rᶜ is aryl or C₁-C₆ alkyl, preferably Rᶜ is phenyl, substituted phenyl or methyl. In a preferred embodiment, R⁴ is —OH. In another embodiment, R⁴ is —N(Rᵇ)R wherein R is —H, aryl or —ORᵇ and Rᵇ is —H, C₁-C₆ alkyl, or C₁-C₆ alkenyl.

In one embodiment, R⁵ is halo, preferably —Br. In a preferred embodiment R⁵ is —H.

Specific examples of compounds of the present invention include the following:

2-(3-tert-butoxycarbonylamino-propylamino)-7-methoxy-quinoline-3-carboxylic acid;
2-(3-amino-propylamino)-7-methoxy-quinoline-3-carboxylic acid;
2-[2-(4-tert-butoxycarbonyl-piperazin-1-yl)-ethylamino]-7-methoxy-quinoline-3-carboxylic acid;
2-(4-tert-butoxycarbonylamino-butyl amino)-7-methoxy-quinoline-3-carboxylic acid;
2-(2-tert-butoxycarbonylamino-ethyl amino)-7-methoxy-quinoline-3-carboxylic acid;
2-(3-dimethylamino-propylamino)-7-methoxy-quinoline-3-carboxylic acid;
2-(2-dimethylamino-ethylamino)-7-methoxy-quinoline-3-carboxylic acid;
2-(2-amino-ethylamino)-7-methoxy-quinoline-3-carboxylic acid;
2-(4-amino-butylamino)-7-methoxy-quinoline-3-carboxylic acid;
2-benzylamino-7-methoxy-quinoline-3-carboxylic acid;
7-methoxy-2-phenethylamino-quinoline-3-carboxylic acid;
7-methoxy-2-(2-pyridin-4-yl-ethylamino)-quinoline-3-carboxylic acid;
2-(2-dimethylamino-ethylamino)-7-methoxy-quinoline-3-carboxylic acid;
2-(indan-2-yl,amino)-7-methoxy-quinoline-3-carboxylic acid;
7-methoxy-2-(3-morpholin-4-yl-propylamino)-quinoline-3-carboxylic acid;
2-(3-diethylamino-propylamino)-7-methoxy-quinoline-3-carboxylic acid;
7-methoxy-2-[3-(2-oxo-pyrrolidin-1-yl)-propylamino]-quinoline-3-carboxylic acid;
2-(4-tert-butyl-benzylamino)-7-methoxy-quinoline-3-carboxylic acid;
7-methoxy-2-[2-(2-oxo-imidazolidin-1-yl)-ethylamino]-quinoline-3-carboxylic acid;
2-(4-dimethylamino-benzylamino)-7-methoxy-quinoline-3-carboxylic acid;
7-methoxy-2-(2-morpholin-4-yl-ethylamino)-quinoline-3-carboxylic acid;
7-methoxy-2-[2-(4-phenoxy-phenyl)-ethylamino]-quinoline-3-carboxylic acid;
2-cyclohexylamino-7-methoxy-quinoline-3-carboxylic acid;
7-methoxy-2-[(tetrahydro-furan-2-ylmethyl)-amino]-quinoline-3-carboxylic acid;
2-(2-hydroxy-ethylamino)-7-methoxy-quinoline-3-carboxylic acid;
2-(2-hydroxy-2-phenyl-ethylamino)-7-methoxy-quinoline-3-carboxylic acid;
2-[2-(3-bromo-4-methoxy-phenyl)-ethylamino]-7-methoxy-quinoline-3-carboxylic acid;
7-methoxy-2-(4-methyl-benzylamino)-quinoline-3-carboxylic acid;
7-methoxy-2-(2-pyridin-3-yl-ethylamino)-quinoline-3-carboxylic acid;
2-[2-(3,4-dimethoxy-phenyl)-ethylamino]-7-methoxy-quinoline-3-carboxylic acid;
2-benzylamino-7-methoxy-quinoline-3-carboxylic acid;
7-methoxy-2-piperidin-1-yl-quinoline-3-carboxylic acid;
7-methoxy-2-(3-pentafluorosulfanyl-phenylamino)-quinoline-3-carboxylic acid;
7-methoxy-2-(5,6,7,8-tetrahydro-naphthalen-1-ylamino)-quinoline-3-carboxylic acid;
7-methoxy-2-(naphthalen-1-ylamino)-quinoline-3-carboxylic acid;
2-[4-(2-diethylamino-ethylcarbamoyl)-phenylamino]-7-methoxy-quinoline-3-carboxylic acid;
2-(3-tert-butoxycarbonylamino-benzylamino)-7-methoxy-quinoline-3-carboxylic acid;
2-(4-tert-butoxycarbonylamino-benzylamino)-7-methoxy-quinoline-3-carboxylic acid;
2-(4-amino-benzylamino)-7-methoxy-quinoline-3-carboxylic acid;
7-methoxy-2-(2,4,6-trimethoxy-benzylamino)-quinoline-3-carboxylic acid;
7-methoxy-2-[3-(3-phenyl-ureido)-benzylamino]-quinoline-3-carboxylic acid;
7-methoxy-2-[4-(3-phenyl-ureido)-benzylamino]-quinoline-3-carboxylic acid;
7-methoxy-2-[4-(toluene-4-sulfonylamino)-benzylamino]-quinoline-3-carboxylic acid;
7-methoxy-2-(3-ureido-benzylamino)-quinoline-3-carboxylic acid;
2-(dimethylaminosulfonylamino-benzylamino)-7-methoxy-quinoline-3-carboxylic acid;
7-methoxy-2-[2-(4-methoxy-phenyl)-ethylamino]-quinoline-3-carboxylic acid;
7-methoxy-2-[2-(2-methoxy-phenyl)-ethylamino]-quinoline-3-carboxylic acid;
7-methoxy-2-(4-methoxy-benzylamino)-quinoline-3-carboxylic acid;

2-[(benzo[1,3]dioxol-5-ylmethyl)-amino]-7-methoxy-quinoline-3-carboxylic acid;
7-methoxy-2-(3-trifluoromethyl-benzylamino)-quinoline-3-carboxylic acid;
7-methoxy-2-[2-(4-nitro-phenyl)-ethylamino]-quinoline-3-carboxylic acid;
2-(3-imidazol-1-yl-propylamino)-7-methoxy-quinoline-3-carboxylic acid;
7-methoxy-2-(4-sulfamoyl-benzylamino)-quinoline-3-carboxylic acid;
7-methoxy-2-(3-methoxy-benzylamino)-quinoline-3-carboxylic acid;
2-(2-chloro-benzylamino)-7-methoxy-quinoline-3-carboxylic acid;
2-[2-(3-fluoro-phenyl)-ethylamino]-7-methoxy-quinoline-3-carboxylic acid;
2-[2-(4-amino-phenyl)-ethylamino]-7-methoxy-quinoline-3-carboxylic acid;
2-(3-amino-benzylamino)-7-methoxy-quinoline-3-carboxylic acid;
2-(2-benzo[1,3]dioxol-5-yl-ethylamino)-7-methoxy-quinoline-3-carboxylic acid;
7-methoxy-2-[2-(3-methoxy-phenyl)-ethylamino]-quinoline-3-carboxylic acid;
2-[2-(3-chloro-phenyl)-ethylamino]-7-methoxy-quinoline-3-carboxylic acid;
7-methoxy-2-[2-(4-sulfamoyl-phenyl)-ethylamino]-quinoline-3-carboxylic acid;
2-[2-(2-chloro-phenyl)-ethylamino]-7-methoxy-quinoline-3-carboxylic acid;
2-[2-(4-hydroxy-phenyl)-ethylamino]-7-methoxy-quinoline-3-carboxylic acid;
2-(3-bromo-benzylamino)-7-methoxy-quinoline-3-carboxylic acid;
2-(3-chloro-benzylamino)-7-methoxy-quinoline-3-carboxylic acid;
7-methoxy-2-(2-piperazin-1-yl-ethylamino)-quinoline-3-carboxylic acid;
7-methoxy-2-[2-(1-methyl-pyrrolidin-2-yl)-ethylamino]-quinoline-3-carboxylic acid;
7-methoxy-2-piperidin-1-yl-quinoline-3-carboxylic acid;
2-(4-chloro-benzylamino)-7-methoxy-quinoline-3-carboxylic acid;
2-(4-hydroxy-piperidin-1-yl)-7-methoxy-quinoline-3-carboxylic acid;
2-(tert-butoxycarbonylmethyl-amino)-7-methoxy-quinoline-3-carboxylic acid;
2-[2-(2-hydroxy-ethoxy)-ethylamino]-7-methoxy-quinoline-3-carboxylic acid;
7-methoxy-2-(3-methoxy-propylamino)-quinoline-3-carboxylic acid;
7-methoxy-2-(2-methoxy-ethylamino)-quinoline-3-carboxylic acid;
2-(3-hydroxy-propylamino)-7-methoxy-quinoline-3-carboxylic acid;
2-(2-carboxy-ethylamino)-7-methoxy-quinoline-3-carboxylic acid;
7-methoxy-2-propylamino-quinoline-3-carboxylic acid;
2-(carboxymethyl-amino)-7-methoxy-quinoline-3-carboxylic acid;
3-(2-chloro-phenylamino)-6-methoxy-naphthalene-2-carboxylic acid;
2-(2-chloro-phenylamino)-7-methoxy-quinoline-3-carboxylic acid phenylamide;
2-(2-chloro-phenylamino)-7-hydroxy-quinoline-3-carboxylic acid phenylamide;
2-(2-chloro-phenylamino)-7-hydroxy-quinoline-3-carboxylic acid;
2-(2-chloro-phenylamino)-7-(2-hydroxy-ethoxy)-quinoline-3-carboxylic acid;
2-(3,4-dichlorophenylamino)-7-methoxy-quinoline-3-carboxylic acid;
2-(3-biphenylamino)-7-methoxy-quinoline-3-carboxylic acid;
7-methoxy-2-(phenylamino)-quinoline-3-carboxylic acid;
7-methoxy-2-(methyl-3-methylphenylamino)-quinoline-3-carboxylic acid;
2-(cyclohexylamino)-7-methoxy-quinoline-3-carboxylic acid;
2-(3-chlorophenylamino)-6,7-dimethoxy-quinoline-3-carboxylic acid;
2-(3-chlorophenylamino)-6,7-methylenedioxy-quinoline-3-carboxylic acid;
2-(3-chlorophenylamino)-7-hydroxy-quinoline-3-carboxylic acid;
8-bromo-2-(3-chlorophenylamino)-7-hydroxy-quinoline-3-carboxylic acid;
2-(3-chlorophenylamino)-7-methoxy-quinoline-3-carboxamide phenylsulphonamide;
2-(3-chlorophenylamino)-7-methoxy-quinoline-3-carboxamide 2-nitro-phenylsulphonamide;
2-(3-chlorophenylamino)-7-methoxy-quinoline-3-carboxamide methylsulphonamide;
8-bromo-2-(3-chlorophenylamino)-7-methoxy-quinoline-3-carboxylic acid;
2-(3-acetophenylamino)-7-methoxy-quinoline-3-carboxylic acid;
2-(2-benzophenone-yl-amino)-7-methoxy-quinoline-3-carboxylic acid;
2-(2-fluoro-5-methylphenylamino)-7-methoxy-quinoline-3-carboxylic acid;
2-(2-cyanophenylamino)-7-methoxy-quinoline-3-carboxylic acid;
2-(2-chloro-6-methylphenylamino)-7-methoxy-quinoline-3-carboxylic acid;
2-(4-carboxybenzylamino)-7-methoxy-quinoline-3-carboxylic acid;
2-(3-chloro-6-methoxyphenylamino)-7-methoxy-quinoline-3-carboxylic acid;
2-(2-ethylphenylamino)-7-methoxy-quinoline-3-carboxylic acid;
7-methoxy-2-(4-nitrophenylamino)-quinoline-3-carboxylic acid;
2-(4-carboxamidophenylamino)-7-methoxy-quinoline-3-carboxylic acid;
7-methoxy-2-(4-hydroxyphenethylamino)-quinoline-3-carboxylic acid; and
7-methoxy-2-(piperidin-4-ol)-quinoline-3-carboxylic acid;

or a salt, solvate, or physiologically functional derivative thereof.

Further specific examples of compounds of the present invention include the following:

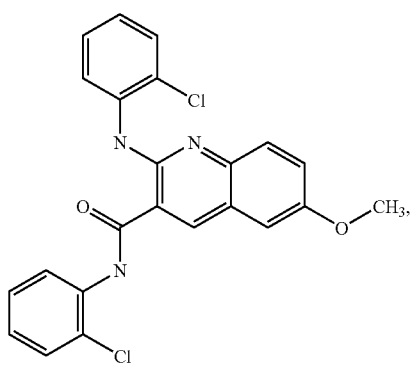
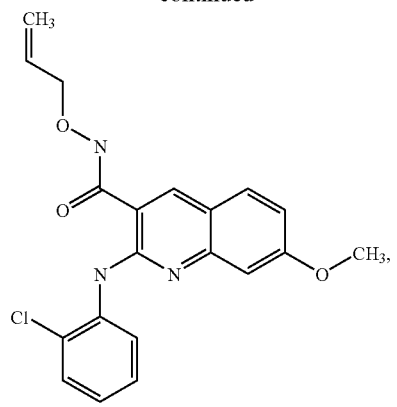
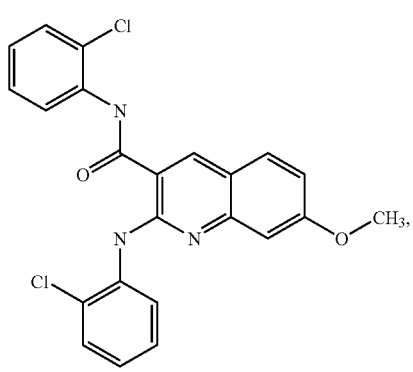
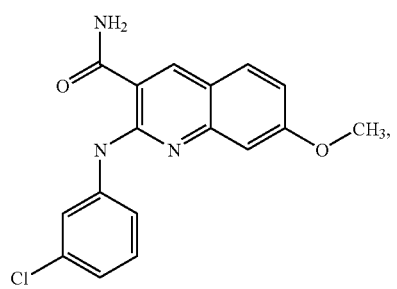
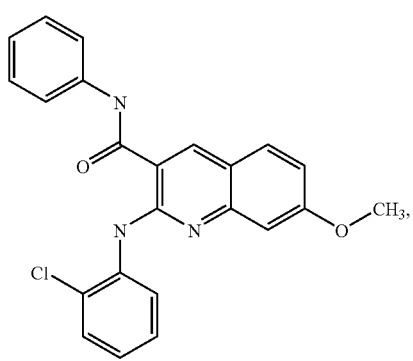
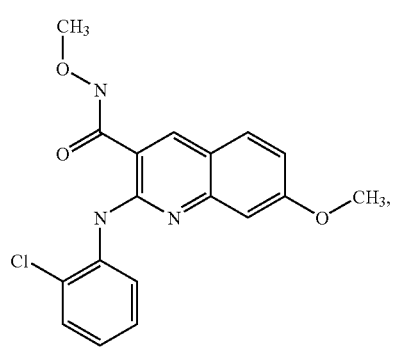
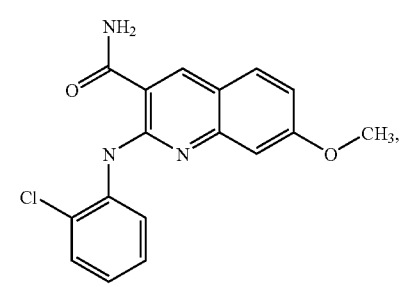
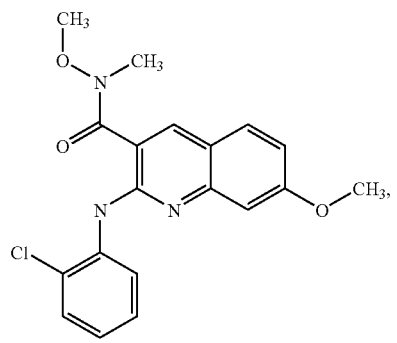

-continued

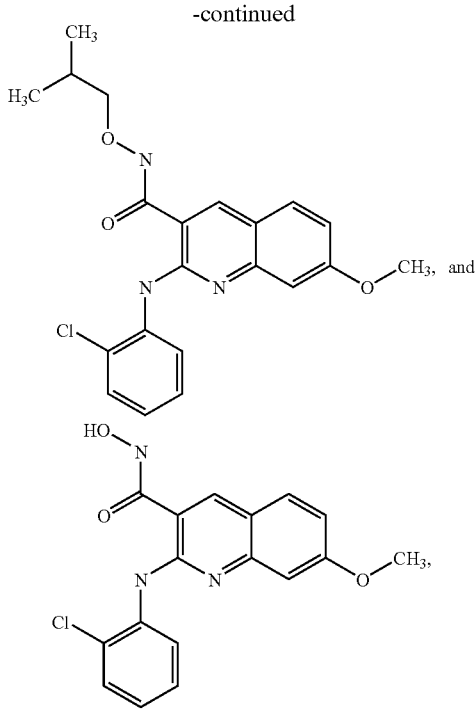

or a salt, solvate, or physiologically functional derivative thereof.

Typically, the salts of the present invention are pharmaceutically acceptable salts. Salts encompassed within the term "pharmaceutically acceptable salts" refer to non-toxic salts of the compounds of this invention. Salts of the compounds of the present invention may comprise acid addition salts derived from a nitrogen on a substituent in the compound of formula (I). Representative salts include the following salts: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate, methylbromide, methylnitrate, methylsulfate, monopotassium maleate, mucate, napsylate, nitrate, N-methylglucamine, oxalate, pamoate (embonate), palmitate, pantothenate, phosphateldiphosphate, polygalacturonate, potassium, salicylate, sodium, stearate, subacetate, succinate, tannate, tartrate, teoclate, tosylate, triethiodide, trimethylammonium and valerate. Other salts, which are not pharmaceutically acceptable, may be useful in the preparation of compounds of this invention and these form a further aspect of the invention.

While it is possible that, for use in therapy, therapeutically effective amounts of a compound of formula (I), as well as salts, solvates and physiological functional derivatives thereof, may be administered as the raw chemical, it is possible to present the active ingredient as a pharmaceutical composition. Accordingly, the invention further provides pharmaceutical compositions, which include therapeutically effective amounts of compounds of the formula (I) and salts, solvates and physiological functional derivatives thereof, and one or more pharmaceutically acceptable carriers, diluents, or excipients. The compounds of the formula (I) and salts, solvates and physiological functional derivatives thereof, are as described above. The carrier(s), diluent(s) or excipient(s) must be acceptable in the sense of being compatible with the other ingredients of the formulation and not deleterious to the recipient thereof. In accordance with another aspect of the invention there is also provided a process for the preparation of a pharmaceutical formulation including admixing a compound of the formula (I), or salts, solvates and physiological functional derivatives thereof, with one or more pharmaceutically acceptable carriers, diluents or excipients.

Pharmaceutical formulations may be presented in unit dose forms containing a predetermined amount of active ingredient per unit dose. Such a unit may contain, for example, 0.5 mg to 1 g, preferably 1 mg to 700 mg, more preferably 5 mg to 100 mg of a compound of the formula (I), depending on the condition being treated, the route of administration and the age, weight and condition of the patient, or pharmaceutical formulations may be presented in unit dose forms containing a predetermined amount of active ingredient per unit dose. Preferred unit dosage formulations are those containing a daily dose or sub-dose, as herein above recited, or an appropriate fraction thereof, of an active ingredient. Furthermore, such pharmaceutical formulations may be prepared by any of the methods well known in the pharmacy art.

Pharmaceutical formulations may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax or the like.

The compounds of formula (I), and salts, solvates and physiological functional derivatives thereof, can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of formula (I) and salts, solvates and physiological functional derivatives thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolylysine substituted with palmitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles and mouth washes.

Pharmaceutical formulations adapted for rectal administration may be presented as suppositories or as enemas.

Pharmaceutical formulations adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists, which may be generated by means of various types of metered, dose pressurised aerosols, nebulizers or insufflators.

Pharmaceutical formulations adapted for vaginal administration may be presented as pessaries, tampons, creams, gels, pastes, foams or spray formulations.

Pharmaceutical formulations adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

It should be understood that in addition to the ingredients particularly mentioned above, the formulations may include other agents conventional in the art having regard to the type of formulation in question, for example those suitable for oral administration may include flavouring agents.

A therapeutically effective amount of a compound of the present invention will depend upon a number of factors including, for example, the age and weight of the animal, the precise condition requiring treatment and its severity, the nature of the formulation, and the route of administration, and will ultimately be at the discretion of the attendant physician or veterinarian. However, an effective amount of a compound of formula (I) for the treatment of neoplastic growth, for example colon or breast carcinoma, will generally be in the range of 0.1 to 100 mg/kg body weight of recipient (mammal) per day and more usually in the range of 1 to 10 mg/kg body weight per day. Thus, for a 70 kg adult mammal, the actual amount per day would usually be from 70 to 700 mg and this amount may be given in a single dose per day or more usually in a number (such as two, three, four, five or six) of sub-doses per day such that the total daily dose is the same. An effective amount of a salt or solvate, or physiologically functional derivative thereof, may be determined as a proportion of the effective amount of the compound of formula (I) per se. It is envisaged that similar dosages would be appropriate for treatment of the other conditions referred to above.

The compounds of formula (I) and salts, solvates and physiological functional derivatives thereof, are believed to have utility in treating conditions of hematopoietic cellular deficiency, such as anemias, including anemias due to renal insufficiency or to chronic disease, such as autoimmunity or cancer, neutropenia, cytopenia, drug-induced anemias, polycythemia, cancer and myelosuppression as a result of inhibition of the protein kinase YAK3.

The present invention thus also provides compounds of formula (I) and pharmaceutically acceptable salts or solvates thereof, or physiologically functional derivatives thereof, for use in medical therapy, and particularly in the treatment of disorders mediated by YAK3 activity.

The inappropriate YAK3 activity referred to herein is any YAK3 activity that deviates from the normal YAK3 activity expected in a particular mammalian subject. Inappropriate YAK3 activity may take the form of, for instance, an abnormal increase in activity, or an aberration in the timing and or control of YAK3 activity. Such inappropriate activity may result then, for example, from overexpression or mutation of the protein kinase leading to inappropriate or uncontrolled activation.

The present invention is directed to methods of regulating, modulating, or inhibiting YAK3 for the prevention and/or treatment of disorders related to unregulated YAK3 activity. In particular, the compounds of the present invention can also be used in the treatment of certain forms of hematopoietic cellular deficiency, such as anemias, including anemias due to renal insufficiency or to chronic disease, such as autoimmunity or cancer, neutropenia, cytopenia, drug-induced anemias, polycythemia, cancer and myelosuppression.

A further aspect of the invention provides a method of treatment of a mammal suffering from a disorder mediated by YAK3 activity, which includes administering to said subject an effective amount of a compound of formula (I) or a pharmaceutically acceptable salt, solvate, or a physiologically functional derivative thereof.

A further aspect of the present invention provides the use of a compound of formula (I), or a pharmaceutically acceptable salt or solvate thereof, or a physiologically functional derivative thereof, in the preparation of a medicament for the treatment of a disorder characterized by inappropriate YAK3 activity.

Certain embodiments of the present invention will now be illustrated by way of example only. The physical data given for the compounds exemplified is consistent with the assigned structure of those compounds.

EXAMPLES

As used herein the symbols and conventions used in these processes, schemes and examples are consistent with those used in the contemporary scientific literature, for example, the *Journal of the American Chemical Society* or the *Journal of Biological Chemistry*. Standard single-letter or three-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

g (grams); mg (milligrams);
L (liters); mL (milliliters);
μL (microliters); psi (pounds per square inch);
M (molar); mM (millimolar);
i. v. (intravenous); Hz (Hertz);
MHz (megahertz); mol (moles);
mmol (millimoles); rt (room temperature);
min (minutes); h (hours);
mp (melting point); TLC (thin layer chromatography);
$T_r$ (retention time); RP (reverse phase);
MeOH (methanol); i-PrOH (isopropanol);
TEA (triethylamine); TFA (trifluoroacetic acid);
TFAA (trifluoroacetic anhydride); THF (tetrahydrofuran);
DMSO (dimethylsulfoxide); AcOEt (ethyl acetate);
DME (1,2-dimethoxyethane); DCM (dichloromethane);
DCE (dichloroethane); DMF (N,N-dimethylformamide);
DMPU (N,N'-dimethylpropyleneurea); CDI (1,1-carbonyldiimidazole);
IBCF (isobutyl chloroformate); HOAc (acetic acid);
HOSu (N-hydroxysuccinimide); HOBT (1-hydroxybenzotriazole);
mCPBA (meta-chloroperbenzoic acid;
EDC (1-[3-dimethylamino) propyl]-3-ethylcarbodiimide hydrochloride);
BOC (tert-butyloxycarbonyl); FMOC (9-fluorenylmethoxycarbonyl);
DCC (dicyclohexylcarbodiimide); CBZ (benzyloxycarbonyl);
Ac (acetyl); atm (atmosphere);
TMSE (2-(trimethylsilyl)ethyl); TMS (trimethylsilyl);
TIPS (triisopropylsilyl); TBS (t-butyldimethylsilyl);
DMAP (4-dimethylaminopyridine); BSA (bovine serum albumin)
ATP (adenosine triphosphate); HRP (horseradish peroxidase);
DMEM (Dulbecco's modified Eagle medium);
HPLC (high pressure liquid chromatography);
BOP (bis(2-oxo-3-oxazolidinyl)phosphinic chloride);
TBAF (tetra-n-butylammonium fluoride);
HBTU(O-Benzotriazole-1-yl-N,N,N',N'-tetramethyluroniumhexafluoro phosphate).
HEPES (4-(2-hydroxyethyl)-1-piperazine ethane sulfonic acid);
DPPA (diphenylphosphoryl azide);
$fHNO_3$ (fuming $HNO_3$); and
EDTA (ethylenediaminetetraacetic acid).

All references to ether are to diethyl ether; brine refers to a saturated aqueous solution of NaCl. Unless otherwise indicated, all temperatures are expressed in ° C. (degrees Centigrade). All reactions are conducted under an inert atmosphere at room temperature unless otherwise noted.

$^1$H NMR spectra were recorded on a Varian VXR-300, a Varian Unity-300, a Varian Unity-400 instrument, a Brucker AVANCE-400, or a General Electric QE-300. Chemical shifts are expressed in parts per million (ppm, δ units). Coupling constants are in units of hertz (Hz). Splitting patterns describe apparent multiplicities and are designated as s (singlet), d (doublet), t (triplet), q (quartet), quint (quintet), m (multiplet), br (broad).

HPLC were recorded on a Gilson HPLC or Shimazu HPLC system by the following conditions. Column: 50×4.6 mm (id) stainless steel packed with 5 μm Phenomenex Luna C-18; Flow rate: 2.0 mL/min; Mobile phase: A phase=50 mM ammonium acetate (pH 7.4), B phase=acetonitrile, 0-0.5 min (A: 100%, B: 0%), 0.5-3.0 min (A:100-0%, B:0-100%), 3.0-3.5 min (A: 0%, B: 100%), 3.5-3.7 min (A: 0-100%, B: 100-0%), 3.7-4.5 min (A: 100%, B: 0%); Detection: UV 254 nm; Injection volume: 3 μL.

Low-resolution mass spectra (MS) were recorded on a JOEL JMS-AX505HA, JOEL SX-102, or a SCIEX-APIiii spectrometer; LC-MS were recorded on a micromass 2MD and Waters 2690; high resolution MS were obtained using a JOEL SX-102A spectrometer. All mass spectra were taken under electrospray ionization (ESI), chemical ionization (CI), electron impact (EI) or by fast atom bombardment (FAB) methods. Infrared (IR) spectra were obtained on a Nicolet 510 FT-IR spectrometer using a 1-mm NaCl cell. Most of the reactions were monitored by thin-layer chromatography on 0.25 mm E. Merck silica gel plates (60F-254), visualized with UV light, 5% ethanolic phosphomolybdic acid or p-anisaldehyde solution. Flash column chromatography was performed on silica gel (230-400 mesh, Merck).

The compounds of this invention may be made by a variety of methods, including standard chemistry. Any previously defined variable will continue to have the previously defined meaning unless otherwise indicated. Illustrative general synthetic methods are set out below and then specific compounds of the invention are prepared in the Working Examples.

Compounds of general formula (I) may be prepared by methods known in the art of organic synthesis as set forth in part by the following synthesis schemes. In all of the schemes described below, it is well understood that protecting groups for sensitive or reactive groups are employed where necessary in accordance with general principles of chemistry. Protecting groups are manipulated according to standard methods of organic synthesis (T. W. Green and P. G. M. Wuts (1991) *Protecting Groups in Organic Synthesis*, John Wiley & Sons). These groups are removed at a convenient stage of the compound synthesis using methods that are readily apparent to those skilled in the art. The selection of processes as well as the reaction conditions and order of their execution shall be consistent with the preparation of compounds of Formula (I). Those skilled in the art will recognize if a stereocenter exists in compounds of Formula (I). Accordingly, the present invention includes both possible stereoisomers and includes not only racemic compounds but the individual enantiomers as well. When a compound is desired as a single enantiomer, it may be obtained by stereospecific synthesis or by resolution of the final product or any convenient intermediate. Resolution of the final product, an intermediate, or a starting material may be effected by any suitable method known in the art. See, for example, *Stereochemistry of Organic Compounds* by E. L. Eliel, S. H. Wilen, and L. N. Mander (Wiley-Interscience, 1994).

Compounds of Formula I can be prepared according to the synthetic sequences illustrated in Schemes 1, 2, 3, 4, and 5 and further detailed in the Examples section following. In general, the synthetic methods used herein are those detailed in J. C. S. Perkin 1, 1981, 5, 1520-30 and *J. Het. Chem.* 1991, 28(5), 1339-40 for preparing substituted carboxy quinolines.

Scheme 1 illustrates a synthetic scheme for the preparation of a 3-carboxyquinoline intermediate useful in the preparation of the compounds of Formula I. Briefly, a substituted aniline (I) is acylated with acetyl chloride in the presence of diethylamine and THF to give the resulting acetanilide (II). Treatment of the acetanilide (II) with POCl$_3$ in DMF gives a 2-chloride-3-formyl quinoline (III). Oxidation with AgNO$_3$ in basic ethanol gives the corresponding 2-chloride-3-carboxy quinoline (IV).

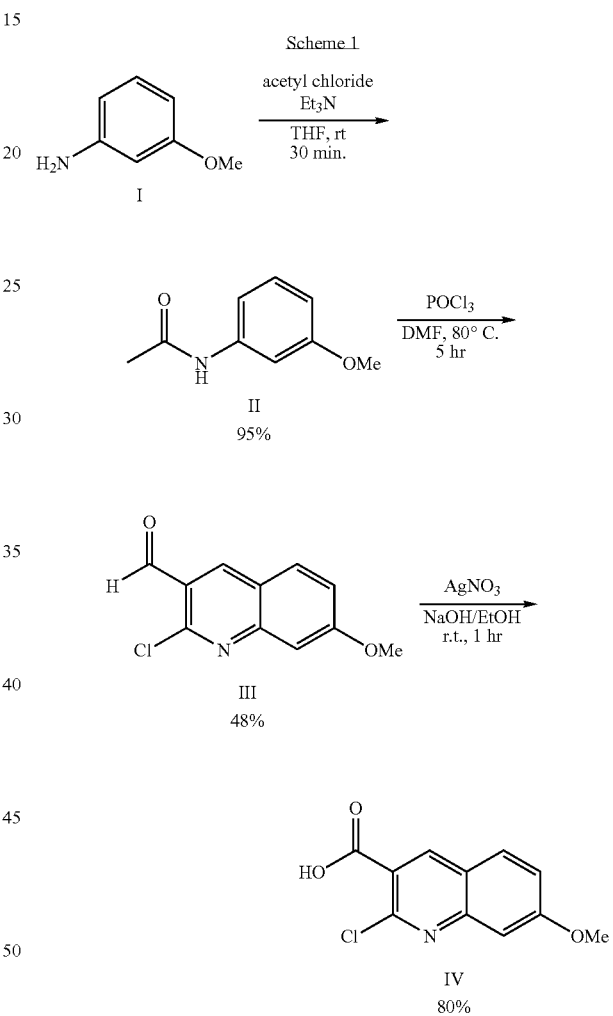

Compounds of Formula (I) having an alkylamine substituent at position R$^2$ may be prepared according to the procedures of Schemes 1 and 2 and Examples 1 and 2.

-continued

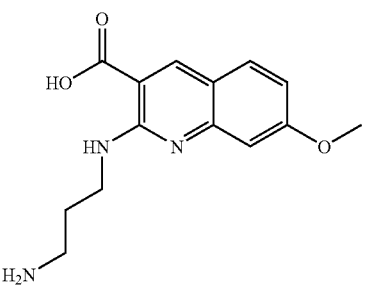

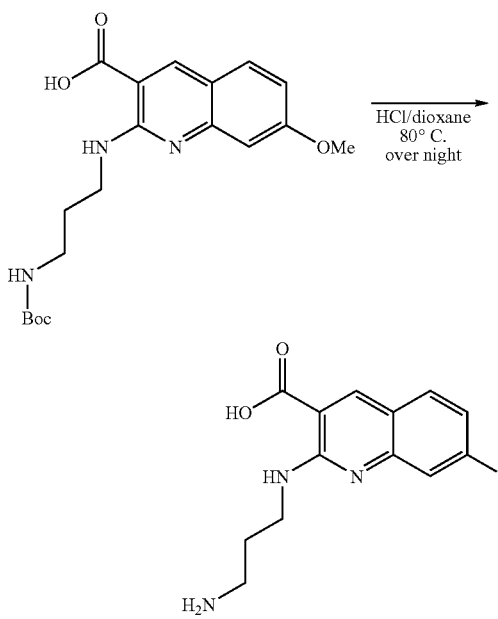

Example 1

2-(3-tert-butoxycarbonylamino-propylamino)-7-methoxy-quinoline-3-carboxylic acid A suspension of 2-Chloro-7-methoxy-quinoline-3-carboxylic acid (60 mg, 0.22 mmol), (3-Amino-propyl)-carbamic acid tert-butyl ester (77 mg, 0.44 mmol), Potassium carbonate (73 mg, 0.46 mmol), and Molecular sieve-4A (300 mg) in dry DMSO (4 ml) was heated at 100° C. for over night. The reaction mixture was purified by chromatography on SCX column using MeOH as eluent and 2-(3-tert-Butoxycarbonylamino-propylamino)-7-methoxy-quinoline-3-carboxylic acid was obtained as white solid after recrystallization from CH$_2$Cl$_2$ and Hexane; 70 mg (85%).

1H NMR (400 MHz, DMSO-d6) ppm 1.38 (s, 9H), 1.73 (m, 2H), 3.02 (q, 2H, J=6.1 Hz), 3.53 (q, 2H, J=6.1 Hz), 3.87 (s, 3H), 6.84 (dd, 1H, J=2.3, 8.8 Hz), 6.93 (br, 1H), 7.71 (d, 1H, J=8.8 Hz), 8.23 (br, 1H), 8.62 (br, 1H), 13.22 (br, 1H). LC/MS: m/z 376 (M+1)$^+$, 374 (M−1)$^−$.

Example 2

2-(3-amino-propylamino)-7-methoxy-quinoline-3-carboxylic acid

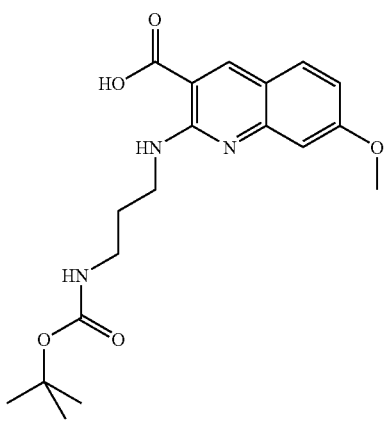

A suspension of 2-(3-tert-Butoxycarbonylamino-propylamino)-7-methoxy-quinoline-3-carboxylic acid (30 mg, 0.08 mmol) in dry 4N HCl/1,4-Dioxane (1 ml) solution was heated at reflux for 5 days. After evaporating the solvent, the residue was recrystallized from methanol and diethyl ether to give 2-(3-Amino-propylamino)-7-methoxy-quinoline-3-carboxylic acid as the white crystal; 19.3 mg (88%). 1H NMR (400 MHz, DMSO-d$_6$) ppm 1.91 (m, 2H), 2.90 (t, 2H, J=7.3 Hz), 3.56 (m, 2H), 3.83 (s, 3H), 6.74 (dd, 1H, J=2.4, 8.6 Hz), 6.88 (d, 1H, J=2.4 Hz), 7.55 (d, 1H, J=8.6 Hz), 8.24 (br, 1H), 8.37 (s, 1H), 10.38 (br, 1H). LC/MS: m/z 276 (M+1)$^+$, 274 (M−1)$^−$.

Additional compounds of formula (I) having an alkylamine R$^2$ substituent or tert-butoxycarbonyl derivative thereof were prepared according to the procedures of Schemes 1 and 2 and Examples 1 and 2 and were characterized as being the following.

2-[2-(4-tert-butoxycarbonyl-piperazin-1-yl)-ethylamino]-7-methoxy-quinoline-3-carboxylic acid;

2-(4-tert-butoxycarbonylamino-butyl amino)-7-methoxy-quinoline-3-carboxylic acid; and 2-(2-tert-butoxycarbonylamino-ethyl amino)-7-methoxy-quinoline-3-carboxylic acid, 2-(2-amino-ethylamino)-7-methoxy-quinoline-3-carboxylic acid; and 2-(4-amino-butylamino)-7-methoxy-quinoline-3-carboxylic acid.

Compounds of Formula (I) having a phenethyl, benzyl, other arylalkyls, heterocyclyl, cycloalkyl, alkylamines or heteroaryl substituent at position R$^2$ may be prepared according to the procedures of Scheme 3 and Examples 3-8. Typically, a suspension of 2-Chloro-7-methoxy-quinoline-3-carboxylic acid (60 mg, 0.22 mmol), the corresponding amine (0.44 mmol), potassium carbonate (73 mg, 0.46 mmol), and molecular sieve-4A (300 mg) in dry DMSO (4 ml) was heated at 100° C. overnight. The reaction mixture was purified by chromatography on SCX column using MeOH as eluent. The corresponding product was obtained usually as white solid after recrystallization from CH$_2$Cl$_2$ and Hexane with good yield. Examples 3-8 as well as the other specifically named compounds were prepared according to the procedures of Schemes 1 and 3.

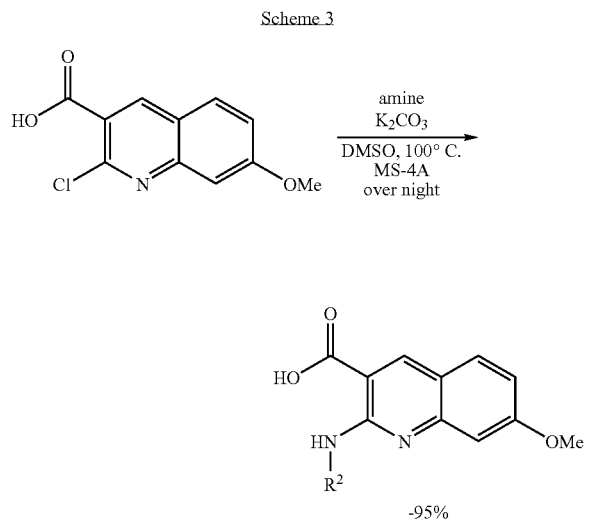

Scheme 3

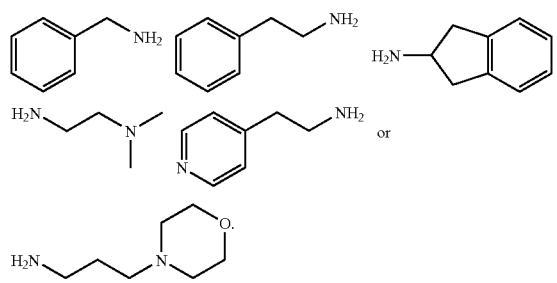

representative amines =

Example 3

2-benzylamino-7-methoxy-quinoline-3-carboxylic acid

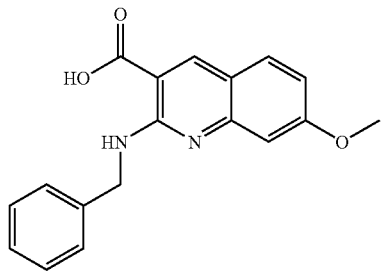

1H NMR (400 MHz, DMSO-d6) ppm 3.87 (s, 3H), 4.79 (d, 2H, J=5.0 Hz), 6.86 (dd, 1H. J=2.5, 8.6 Hz), 6.92 (d, 1H, J=2.5 Hz), 7.25 (t, 1H, J=7.1 Hz), 7.32~7.42 (m, 4H), 7.74 (d, 1H, J=8.8 Hz), 8.58 (br, 1H), 8.67 (s, 1H). LC/MS: m/z 309 (M+1)$^+$, 307 (M−1)$^-$.

Example 4

7-methoxy-2-phenethylamino-quinoline-3-carboxylic acid

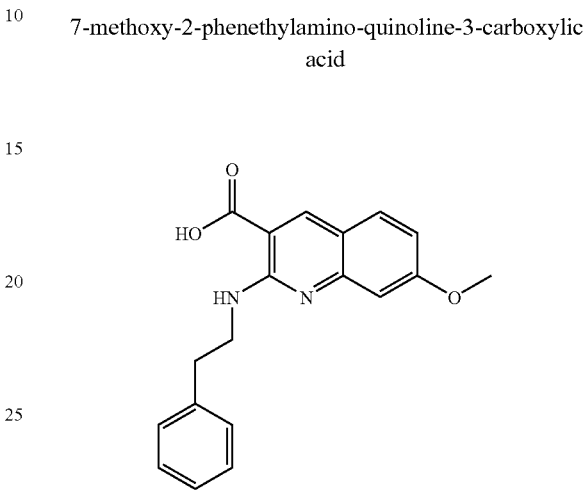

1H NMR (400 MHz, DMSO-d6) ppm 2.95 (t, 2H, J=7.0 Hz), 3.76 (dt, 2H, J=5.3, 7.0 Hz), 3.88 (s, 3H), 6.85 (dd, 1H, J=2.3, 8.8 Hz), 6.96 (s, 1H), 7.21 (m, 1H), 7.24~7.33 (m, 4H), 7.71 (d, 1H, J=8.8 Hz), 8.27 (br, 1H), 8.62 (s, 1H). LC/MS: m/z 323 (M+1)$^+$, 321 (M−1)$^-$.

Example 5

7-methoxy-2-(2-pyridin-4-yl-ethylamino)-quinoline-3-carboxylic acid

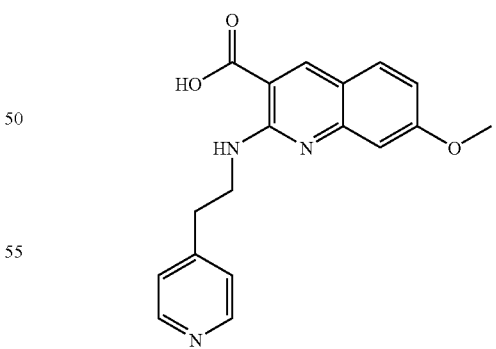

1H NMR (400 MHz, DMSO-d6) ppm 2.98 (t, 2H, J=7.0 Hz), 3.81 (m, 2H), 3.89 (s, 3H), 6.85 (dd, 1H, J=2.0, 8.6 Hz), 6.96 (s, 1H), 7.33 (d, 2H, J=4.6 Hz), 7.70 (d, 1H, J=8.6 Hz), 8.33(br, 1H), 8.48(d, 2H, J=4.6 Hz), 8.62 (s, 1H), 13.23 (br, 1H). LC/MS: m/z 324 (M+1)$^+$, 322 (M−1)$^-$.

Example 6

2-(2-dimethylamino-ethylamino)-7-methoxy-quinoline-3-carboxylic acid hydrochloride

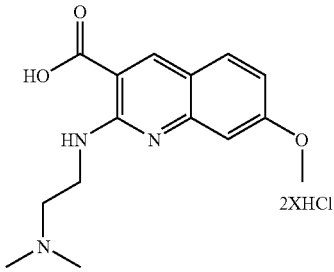

1H NMR (400 MHz, DMSO-d6, 333K) ppm 2.88 (s, 6H), 3.41 (t, 2H, J=6.1 Hz), 3.91 (s, 3H), 4.05 (br, 2H), 6.98 (dd, 1H, J=2.3, 8.8 Hz), 7.32 (br, 1H), 7.82 (d, 1H, J=8.8 Hz), 8.77 (s, 1H). LC/MS: m/z 290 (M+1)$^+$, 288 (M−1)$^-$.

Example 7

2-(indan-2-ylamino)-7-methoxy-quinoline-3-carboxylic acid

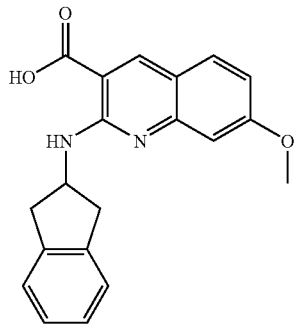

1H NMR (400 MHz, DMSO-d$_6$) ppm 2.90 (dd, 2H, J=5.6, 15.9 Hz), 3.40 (shielded by H2O peak in DMSO-d6, 2H), 3.89 (s, 3H), 4.96 (m, 1H), 6.86 (dd, 1H, J=2.5, 8.8 Hz), 6.98 (d, 1H, J=2.5 Hz), 7.17 (m, 2H), 7.28 (m, 2H), 7.74 (d, 1H, J=8.8 Hz), 8.55 (br, 1H), 8.64 (s 1H). LC/MS: m/z 335 (M+1)$^+$, 333 (M−1)$^-$.

Example 8

7-methoxy-2-(3-morpholin-4-yl-propylamino)-quinoline-3-carboxylic acid

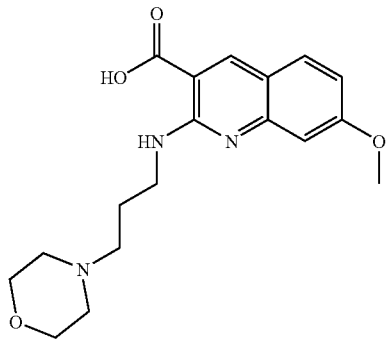

1H NMR (400 MHz, DMSO-d6) ppm 1.80 (quintet, 2H, J=6.8 Hz), 2.46 (m, 6H), 3.57 (t, 2H, J=6.8 Hz), 3.62 (t, 4H, J=4.5 Hz), 3.87 (s, 3H), 6.83 (dd, 1H, J=2.2, 8.8 Hz), 6.90 (d, 1H, J=2.2 Hz), 7.69 (d, 1H, J=8.8 Hz), 8.60 (s 1H). LC/MS: m/z 346 (M+1)$^+$, 344 (M−1)$^-$.

Additional compounds of formula (I) having a phenethyl, benzyl, heterocyclyl, cycloalkyl, alkylamine, or heteroaryl R$^2$ substituent were prepared according to the procedures of Schemes 1 and 3 and were characterized as being the following.

7-methoxy-2-[3-(2-oxo-pyrrolidin-1-yl)-propylamino]-quinoline-3-carboxylic acid;

2-(4-tert-butyl-benzylamino)-7-methoxy-quinoline-3-carboxylic acid;

7-methoxy-2-[2-(2-oxo-imidazolidin-1-yl)-ethylamino]-quinoline-3-carboxylic acid;

2-(4-dimethylamino-benzylamino)-7-methoxy-quinoline-3-carboxylic acid;

7-methoxy-2-(2-morpholin-4-yl-ethylamino)-quinoline-3-carboxylic acid;

7-methoxy-2-[2-(4-phenoxy-phenyl)-ethylamino]-quinoline-3-carboxylic acid;

2-cyclohexylamino-7-methoxy-quinoline-3-carboxylic acid;

7-methoxy-2-[(tetrahydro-furan-2-ylmethyl)-amino]-quinoline-3-carboxylic acid;

2-(2-hydroxy-ethylamino)-7-methoxy-quinoline-3-carboxylic acid;

2-(2-hydroxy-2-phenyl-ethylamino)-7-methoxy-quinoline-3-carboxylic acid;

2-[2-(3-bromo-4-methoxy-phenyl)-ethylamino]-7-methoxy-quinoline-3-carboxylic acid;

7-methoxy-2-(4-methyl-benzylamino)-quinoline-3-carboxylic acid;

7-methoxy-2-(2-pyridin-3-yl-ethylamino)-quinoline-3-carboxylic acid;

2-[2-(3,4-dimethoxy-phenyl)-ethylamino]-7-methoxy-quinoline-3-carboxylic acid;

2-benzylamino-7-methoxy-quinoline-3-carboxylic acid;

7-methoxy-2-[2-(4-methoxy-phenyl)-ethylamino]-quinoline-3-carboxylic acid;

7-methoxy-2-[2-(2-methoxy-phenyl)-ethylamino]-quinoline-3-carboxylic acid;

7-methoxy-2-(4-methoxy-benzylamino)-quinoline-3-carboxylic acid;

2-[(benzo[1,3]dioxol-5-ylmethyl)-amino]-7-methoxy-quinoline-3-carboxylic acid;

7-methoxy-2-(3-trifluoromethyl-benzylamino)-quinoline-3-carboxylic acid;

7-methoxy-2-[2-(4-nitro-phenyl)-ethylamino]-quinoline-3-carboxylic acid;

2-(3-imidazol-1-yl-propylamino)-7-methoxy-quinoline-3-carboxylic acid;

7-methoxy-2-(4-sulfamoyl-benzylamino)-quinoline-3-carboxylic acid;

7-methoxy-2-(3-methoxy-benzylamino)-quinoline-3-carboxylic acid;

2-(2-chloro-benzylamino)-7-methoxy-quinoline-3-carboxylic acid;

2-[2-(3-fluoro-phenyl)-ethylamino]-7-methoxy-quinoline-3-carboxylic acid;

2-[2-(4-amino-phenyl)-ethylamino]-7-methoxy-quinoline-3-carboxylic acid;

2-(3-amino-benzylamino)-7-methoxy-quinoline-3-carboxylic acid;

2-(2-benzo[1,3]dioxol-5-yl-ethylamino)-7-methoxy-quinoline-3-carboxylic acid;

7-methoxy-2-[2-(3-methoxy-phenyl)-ethylamino]-quinoline-3-carboxylic acid;

2-[2-(3-chloro-phenyl)-ethylamino]-7-methoxy-quinoline-3-carboxylic acid;

7-methoxy-2-[2-(4-sulfamoyl-phenyl)-ethylamino]-quinoline-3-carboxylic acid;

2-[2-(2-chloro-phenyl)-ethylamino]-7-methoxy-quinoline-3-carboxylic acid;

2-[2-(4-hydroxy-phenyl)-ethylamino]-7-methoxy-quinoline-3-carboxylic acid;

2-(3-bromo-benzylamino)-7-methoxy-quinoline-3-carboxylic acid;

2-(3-chloro-benzylamino)-7-methoxy-quinoline-3-carboxylic acid;

7-methoxy-2-(2-piperazin-1-yl-ethylamino)-quinoline-3-carboxylic acid;

7-methoxy-2-[2-(1-methyl-pyrrolidin-2-yl)-ethylamino]-quinoline-3-carboxylic acid HCl;

7-methoxy-2-(3-morpholin-4-yl-propylamino)-quinoline-3-carboxylic acid; and 7-methoxy-2-piperidin-1-yl-quinoline-3-carboxylic acid;

7-methoxy-2-(3-pentafluorosulfanyl-phenylamino)-quinoline-3-carboxylic acid;

7-methoxy-2-(5,6,7,8-tetrahydro-naphthalen-1-ylamino)-quinoline-3-carboxylic acid;

7-methoxy-2-(naphthalen-1-ylamino)-quinoline-3-carboxylic acid;

2-[4-(2-diethylamino-ethylcarbamoyl)-phenylamino]-7-methoxy-quinoline-3-carboxylic acid;

2-(3-tert-butoxycarbonylamino-benzylamino)-7-methoxy-quinoline-3-carboxylic acid;

2-(4-tert-butoxycarbonylamino-benzylamino)-7-methoxy-quinoline-3-carboxylic acid;

2-(4-amino-benzylamino)-7-methoxy-quinoline-3-carboxylic acid;

7-methoxy-2-(2,4,6-trimethoxy-benzylamino)-quinoline-3-carboxylic acid;

7-methoxy-2-[3-(3-phenyl-ureido)-benzylamino]-quinoline-3-carboxylic acid;

7-methoxy-2-[4-(3-phenyl-ureido)-benzylamino]-quinoline-3-carboxylic acid;

7-methoxy-2-[4-(toluene-4-sulfonylamino)-benzylamino]-quinoline-3-carboxylic acid;

2-(4-chloro-benzylamino)-7-methoxy-quinoline-3-carboxylic acid;

2-(4-carboxy-benzylamino)-7-methoxy-quinoline-3-carboxylic acid;

2-(4-hydroxy-piperidin-1-yl)-7-methoxy-quinoline-3-carboxylic acid;

2-(3-diethylamino-propylamino)-7-methoxy-quinoline-3-carboxylic acid HCl.

2-(3-dimethylamino-propylamino)-7-methoxy-quinoline-3-carboxylic acid HCl;

2-(2-dimethylamino-ethylamino)-7-methoxy-quinoline-3-carboxylic acid HCl;

7-methoxy-2-(3-ureido-benzylamino)-quinoline-3-carboxylic acid; and 2-(dimethylaminosulfonylamino-benzylamino)-7-methoxy-quinoline-3-carboxylic acid.

Additional methods for preparing compounds of formula (I) wherein $R^2$ is an aryl or alkyl group and $R^3$ is as defined above are depicted in Schemes 4-6 and are specifically discussed in International Application PCT/US02/10657 on pages 17-19.

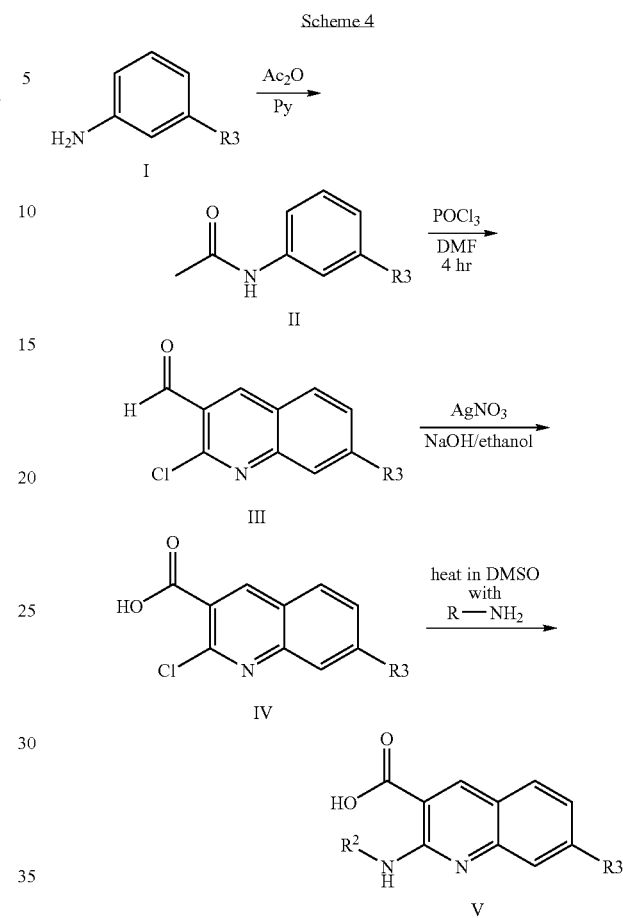

In general, the synthetic methods used herein are those detailed in *J. C. S. Perkin* 1, 1981, 5, 1520-30 and *J. Het. Chem.* 1991, 28(5), 1339-40 for preparing substituted carboxy quinolines. Briefly, a substituted aniline (I) is acylated with acetic anhydride in pyridine to give the resulting acetanilide (II). Treatment of the acetanilide (II) with $POCl_3$ in DMF gives a 2-chloride-3-formyl quinoline (III). Oxidation with $AgNO_3$ in basic ethanol gives the corresponding 2-chloride-3-carboxy quinoline (IV). The 2-chloro can be replaced with an appropriate amines in DMSO to give the resulting 2-substituted quinoline (V) (Scheme 1).

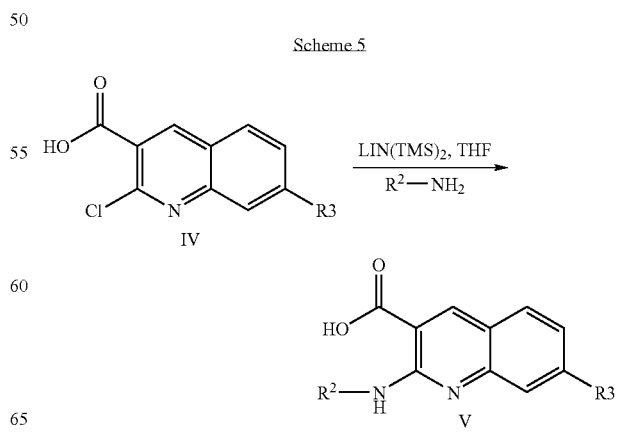

Alternatively, the method of Scheme 5 may be used, in which the 2-chloride-3-carboxy quinoline (IV) is treated with an aryl amine in the presence of excess of lithium hexamethyldisilazane in THF (−70 C to RT) to give the 2-substituted quinoline (V) (Scheme 2). For alkyl amines, excess of the lithium salt of the particular alkyl amine is used in place of lithium hexamethyldisilazane.

Additional compounds of formula (I) having an alkyl, aryl, or other appropriate $R^2$ substituent were prepared according to the procedures of Schemes 4 and 5 and were characterized as the following.

2-(tert-butoxycarbonylmethyl-amino)-7-methoxy-quinoline-3-carboxylic acid;
2-[2-(2-hydroxy-ethoxy)-ethylamino]-7-methoxy-quinoline-3-carboxylic acid;
7-methoxy-2-(3-methoxy-propylamino)-quinoline-3-carboxylic acid;
7-methoxy-2-(2-methoxy-ethylamino)-quinoline-3-carboxylic acid;
2-(3-hydroxy-propylamino)-7-methoxy-quinoline-3-carboxylic acid;
2-(2-carboxy-ethylamino)-7-methoxy-quinoline-3-carboxylic acid;
7-methoxy-2-propylamino-quinoline-3-carboxylic acid;
2-(carboxymethyl-amino)-7-methoxy-quinoline-3-carboxylic acid;
2-(3,4-dichlorophenylamino)-7-methoxy-quinoline-3-carboxylic acid;
2-(3-biphenylamino)-7-methoxy-quinoline-3-carboxylic acid;
7-methoxy-2-(phenylamino)-quinoline-3-carboxylic acid;
7-methoxy-2-(methyl-3-methylphenylamino)-quinoline-3-carboxylic acid;
2-(cyclohexylamino)-7-methoxy-quinoline-3-carboxylic acid;
2-(3-chlorophenylamino)-6,7-dimethoxy-quinoline-3-carboxylic acid;
2-(3-chlorophenylamino)-6,7-methylenedioxy-quinoline-3-carboxylic acid;
2-(3-chlorophenylamino)-7-hydroxy-quinoline-3-carboxylic acid;
8-bromo-2-(3-chlorophenylamino)-7-hydroxy-quinoline-3-carboxylic acid;
2-(3-chlorophenylamino)-7-methoxy-quinoline-3-carboxamide phenylsulphonamide;
2-(3-chlorophenylamino)-7-methoxy-quinoline-3-carboxamide 2-nitro-phenylsulphonamide;
2-(3-chlorophenylamino)-7-methoxy-quinoline-3-carboxamide methylsulphonamide;
8-bromo-2-(3-chlorophenylamino)-7-methoxy-quinoline-3-carboxylic acid;
2-(3-acetophenylamino)-7-methoxy-quinoline-3-carboxylic acid;
2-(2-benzophenone-yl-amino)-7-methoxy-quinoline-3-carboxylic acid;
2-(2-fluoro-5-methylphenylamino)-7-methoxy-quinoline-3-carboxylic acid;
2-(2-cyanophenylamino)-7-methoxy-quinoline-3-carboxylic acid;
2-(2-chloro-6-methylphenylamino)-7-methoxy-quinoline-3-carboxylic acid;
2-(4-carboxybenzylamino)-7-methoxy-quinoline-3-carboxylic acid;
2-(3-chloro-6-methoxyphenylamino)-7-methoxy-quinoline-3-carboxylic acid;
2-(2-ethylphenylamino)-7-methoxy-quinoline-3-carboxylic acid;
7-methoxy-2-(4-nitrophenylamino)-quinoline-3-carboxylic acid;
2-(4-carboxamidophenylamino)-7-methoxy-quinoline-3-carboxylic acid;
7-methoxy-2-(4-hydroxyphenethylamino)-quinoline-3-carboxylic acid; and
7-methoxy-2-(piperidin-4-ol)-quinoline-3-carboxylic acid.

Compounds of Formula (I) having a substituted aryl substituent at position $R^2$ as well as phenyl amide derivatives thereof may be prepared according to the procedures of Scheme 7 and Examples 9-12.

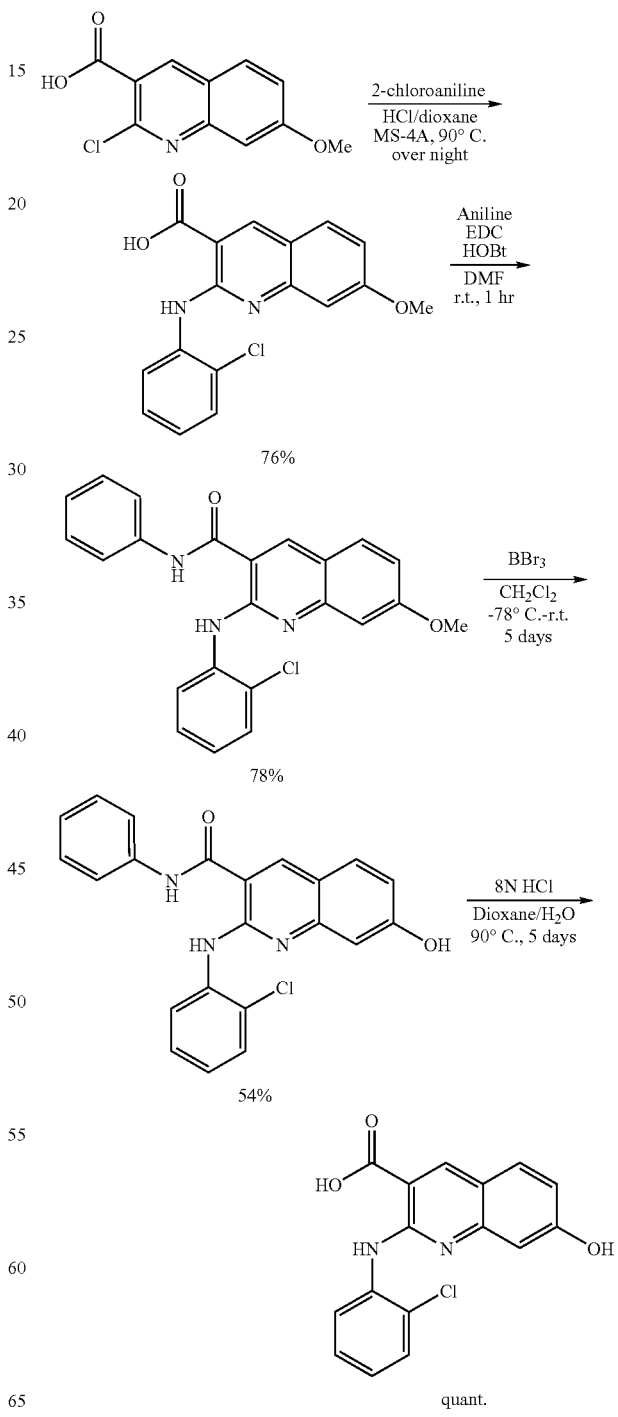

Scheme 7

Example 9

3-(2-Chloro-phenylamino)-6-methoxy-naphthalene-2-carboxylic acid

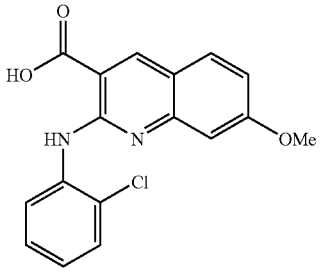

This compound has been prepared in 76% yield via the method exemplified in the first step of Scheme 7.

Example 10

2-(2-Chloro-phenylamino)-7-methoxy-quinoline-3-carboxylic acid phenylamide

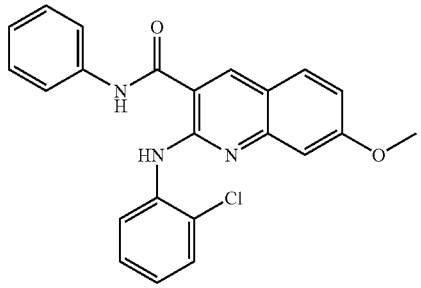

EDC (633 mg, 3.3 mmol) was added to a solution of 2-(2-Chloro-phenylamino)-7-methoxy-quinoline-3-carboxylic acid (986 mg, 3.0 mmol), HOBt (446 mg, 3.3 mmol) and aniline (307 mg, 3.3 mmol) in DMF (5 ml) at room temperature. After stirring the mixture for 1 hr, $CH_2Cl_2$ was used to extract the reaction mixture, and washed with water, saturated brine and then dried with magnesium sulfate. The solvent was removed under reduced pressure to give yellow oil. The yellow oil was purified by chromatography on SCX column using MeOH as eluent. At last, 2-(2-Chloro-phenylamino)-7-hydroxy-quinoline-3-carboxylic acid phenylamide was obtained as yellow solid after recrystallization from $CH_2Cl_2$ and Hexane; 947 mg (78%).

Example 11

2-(2-Chloro-phenylamino)-7-hydroxy-quinoline-3-carboxylic acid phenylamide

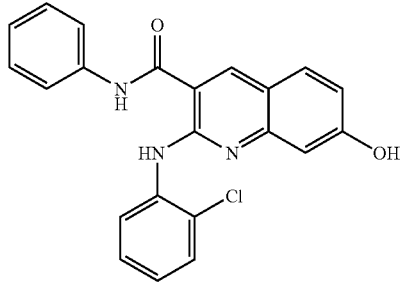

2-(2-Chloro-phenylamino)-7-methoxy-quinoline-3-carboxylic acid phenylamide (404 mg, 1.0 mmol) was dissolved in dry $CH_2Cl_2$ (5 ml). After cooling to −78° C., 1.0 N BBr3 (5.0 ml, 5.0 mmol) in $CH_2Cl_2$ was dropped into the above solution over 5 min. The reaction mixture was allowed to warm to room temperature over 1 hr and stirred for 5 days. $CH_2Cl_2$ was added to extract the reaction mixture, and washed with water, saturated brine and then dried with magnesium sulfate. After evaporating the solvent under reduced pressure, the residue was purified by chromatography on SCX column using MeOH as eluent. At last, 2-(2-Chloro-phenylamino)-7-hydroxy-quinoline-3-carboxylic acid phenylamide was obtained as yellow solid after recrystallization from $CH_2Cl_2$ and Hexane; 210 mg (54%).

Example 12

2-(2-Chloro-phenylamino)-7-hydroxy-quinoline-3-carboxylic acid

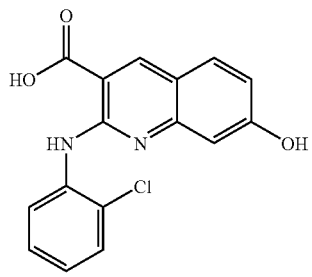

A suspension of 2-(2-Chloro-phenylamino)-7-hydroxy-quinoline-3-carboxylic acid phenylamide (17 mg, 0.04 mmol) in 16N aqueous HCl (0.1 ml) and 1,4-Dioxane (0.1 ml) was heated at reflux for 5 days. After evaporating the solvent, the residue was recrystallized from methanol to give 2-(2-Chloro-phenylamino)-7-hydroxy-quinoline-3-carboxylic acid as the white crystal; 13 mg (99%). 1H NMR (400 MHz, DMSO-d6) ppm 6.96 (dd, 1H, J=2.3, 8.6 Hz), 6.99 (d, 1H. J=2.3 Hz), 7.04 (ddd, 1H, J=1.5, 7.8, 8.8 Hz), 7.40 (ddd, 1H, J=1.5, 7.8, 8.8 Hz), 7.52 (dd, 1H, J=1.5, 7.8 Hz), 7.83 (d, 1H, J=8.8 Hz), 8.84 (s, 1H), 9.10 (d, 1H, J=11.2 Hz), 10.48 (s, 1H), 11.05 (s, 1H). LC/MS: m/z 315 $(M+1)^+$, 313 $(M-1)^-$.

Additional compounds of formula (I) were prepared according to the procedures of Scheme 7 and were characterized as being the following.

2-(2-Chloro-phenylamino)-7-hydroxy-quinoline-3-carboxylic acid; and 2-(2-Chloro-phenylamino)-7-(2-hydroxy-ethoxy)-quinoline-3-carboxylic acid.

Further additional compounds of formula (I) were prepared according to the procedures of Scheme 1, 2, 3, 4, 5, 6, and/or 7 as appropriate and were characterized as being the following:

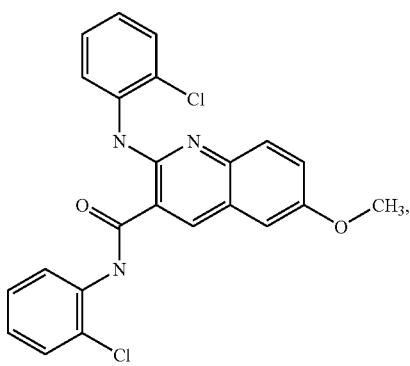

-continued

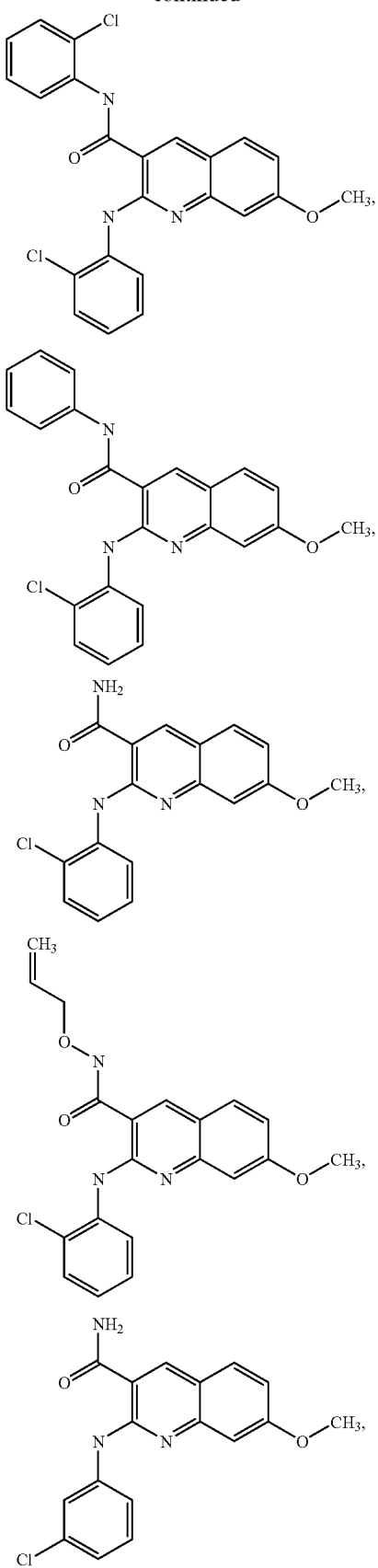

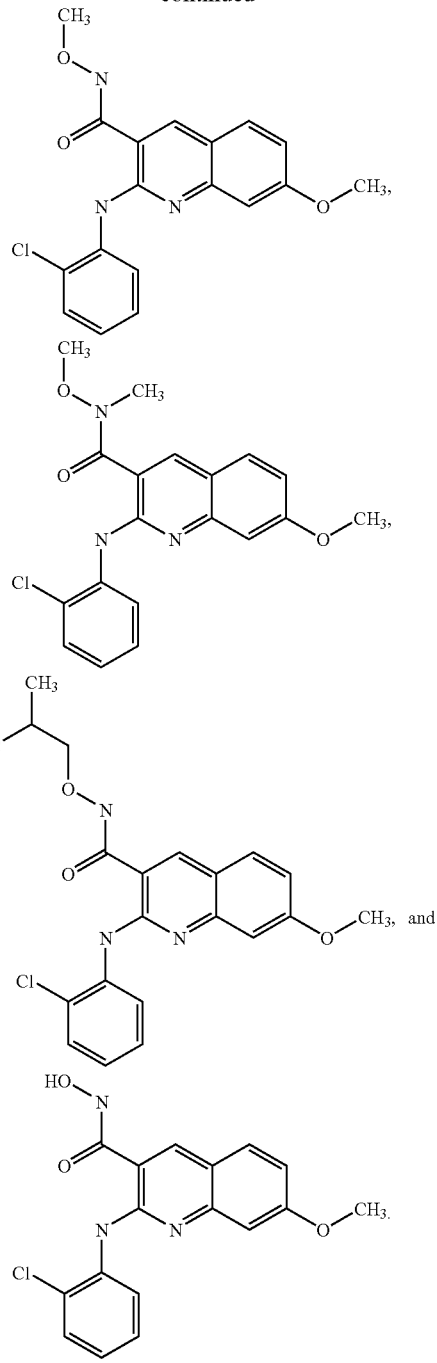

Biological Data

YAK3 Scintillation Proximity Assays Using Ser164 of Myelin Basic Protein as the Phosphoacceptor Source of Ser164 Substrate Peptide:
The biotinylated Ser164, S164A peptide(Biotinyl-LGGRDSRAGS*PMARR—OH), sequence derived from the C-terminus of bovine myelin basic protein (MBP) with Ser162 substituted as Ala162, was purchased from California Peptide Research Inc. (Napa, Calif.), and its purity was determined by HPLC. Phosphorylation occurs at position 164 (marked S* above). The calculated molecular mass of the peptide was 2166 dalton. Solid sample was dissolved at 10 mM in DMSO, aliquoted, and stored at −20° C. until use.

Source of Enzyme:

hYAK3: Glutathione-S-Transferase (GST)-hYak3-His6 containing amino acid residues 124-526 of human YAK3 was purified from baculovirus expression system in Sf9 cells using Glutathione Sepharose 4B column chromatography followed by Ni-NTA-Agarose column chromatography. Purity greater than 65% typically was achieved. Samples, in 50 mM Tris, 150 mM NaCl, 10% glycerol, 0.1% Triton, 250 mM imidazole, 10 mM β-mercapto ethanol, pH 8.0.

were stored at −80° C. until use.

Kinase Assay of Purified hYAK3:

Assays were performed in 96 well (Costar, Catalog No. 3789) or 384 well plates (Costar, Catalog No. 3705). Reaction (in 20, 25, or 40 μl volume) mix contained in final concentrations 25 mM Hepes buffer, pH 7.4; 10 mM $MgCl_2$; 10 mM β-mercapto ethanol; 0.0025% Tween-20; 0.001 mM ATP, 0.1 ⌷Ci of [⌷-$^{33}$P]ATP; purified hYAK3 (7-14 ng/assay; 4 nM final); and 4 μM Ser164 peptide. Compounds, titrated in DMSO, were evaluated at concentrations ranging from 50 μM to 0.5 nM. Final assay concentrations of DMSO did not exceed 5%, resulting in less than 15% loss of YAK3 activity relative to controls without DMSO. Reactions were incubated for 2 hours at room temperature and were stopped by a 75 ul addition of 0.19 μg Streptavidin Scintillation Proximity beads (Amersham Pharmacia Biotech, Catalog No. RPNQ 0007) in PBS, pH 7.4, 10 mM EDTA, 0.1% Triton X-100, 1 mM ATP. Under the assay conditions defined above, the $K_m$(apparent) for ATP was determined to be 7.2+/−2.4 μM. Assay results are depicted in Table 1.

TABLE I

| Ex. No | YAK3 |
|---|---|
| 1 | ++ |
| 2 | +++ |
| 3 | +++ |
| 4 | +++ |
| 5 | +++ |
| 6 | +++ |
| 7 | +++ |
| 8 | ++ |
| 12 | +++ |

+ = p$IC_{50}$ of 4.0-5.0;
++ = p$IC_{50}$ of 5.0-6.0;
+++ = p$IC_{50}$ of >6.0;

We claim:

1. A compound selected from the group consisting of:
2-(3-tert-butoxycarbonylamino-propylamino)-7-methoxy-quinoline-3-carboxylic acid;
2-(3-amino-propylamino)-7-methoxy-quinoline-3-carboxylic acid;
2-[2-(4-tert-butoxycarbonyl-piperazin-1-yl)-ethylamino]-7-methoxy-quinoline-3carboxylic acid;
2-(4-tert-butoxycarbonylamino-butylamino)-7-methoxy-quinoline-3-carboxylic acid;
2-(2-tert-butoxycarbonylamino-ethylamino)-7-methoxy-quinoline-3-carboxylic acid;
2-(3-dimethylamino-propylamino)-7-methoxy-quinoline-3-carboxylic acid;
2-(2-dimethylamino-ethylamino)-7-methoxy-quinoline-3-carboxylic acid;
2-(2-amino-ethylamino)-7-methoxy-quinoline-3-carboxylic acid;
2-(4-amino-butylamino)-7-methoxy-quinoline-3-carboxylic acid;
2-benzylamino-7-methoxy-quinoline-3-carboxylic acid;
7-methoxy-2-phenethylamino-quinoline-3-carboxylic acid;
7-methoxy-2-(2-pyridin-4-yl-ethylamino)-quinoline-3-carboxylic acid;
2-(2-dimethylamino-ethylamino)-7-methoxy-quinoline-3-carboxylic acid;
2-(indan-2-ylamino)-7-methoxy-quinoline-3-carboxylic acid;
7-methoxy-2-(3-morpholin-4-yl-propylamino)-quinoline-3-carboxylic acid;
2-(3-diethylamino-propylamino)-7-methoxy-quinoline-3-carboxylic acid;
7-methoxy-2-[3-(2-oxo-pyrrolidin-1-yl)-propylamino]-quinoline-3-carboxylic acid
2-(4-tert-butyl-benzylamino)-7-methoxy-quinoline-3-carboxylic acid;
7-methoxy-2-[2-(2-oxo-imidazolidin-1-yl)-ethylamino]-quinoline-3-carboxylic acid
2-(4-dimethylamino-benzylamino)-7-methoxy-quinoline-3-carboxylic acid;
7-methoxy-2-(2-morpholin-4-yl-ethylamino)-quinoline-3-carboxylic acid;
7-methoxy-2-[2-(4-phenoxy-phenyl)-ethylamino]-quinoline-3-carboxylic acid;
2-cyclohexylamino-7-methoxy-quinoline-3-carboxylic acid;
7-methoxy-2-[(tetrahydro-furan-2-ylmethyl)-amino]-quinoline-3-carboxylic acid;
2-(2-hydroxy-ethylamino)-7-methoxy-quinoline-3-carboxylic acid;
2-(2-hydroxy-2-phenyl-ethylamino)-7-methoxy-quinoline-3-carboxylic acid;
2-[2-(3-bromo-4-methoxy-phenyl)-ethylamino]-7-methoxy-quinoline-3-carboxylic acid;
7-methoxy-2-(4-methyl-benzylamino)-quinoline-3-carboxylic acid;
7-methoxy-2-(2-pyridin-3-yl-ethylamino)-quinoline-3-carboxylic acid;
2-[2-(3,4-dimethoxy-phenyl)-ethylamino]-7-methoxy-quinoline-3-carboxylic acid;
2-benzylamino-7-methoxy-quinoline-3-carboxytic acid;
7-methoxy-2-(3-morpholin-4-yl-propylamino)-quinoline-3-carboxylic acid;
7-methoxy-2-piperidin-1-yl-quinoline-3-carboxylic acid;
7-methoxy-2-(3-pentafluorosulfanyl-phenylamino)-quinoline-3-carboxylic acid;
7-methoxy-2-(5,6,7,8-tetrahydro-naphthalen-1-ylamino)-quinoline-3-carboxylic acid;
7-methoxy-2-(naphthalen-1-ylamino)-quinoline-3-carboxylic acid;
2-[4-(2-diethylamino-ethylcarbamoyl)-phenylamino]-7-methoxy-quinoline-3-carboxylic acid;
2-(3-tert-butoxycarbonylamino-benzylamino)-7-methoxy-quinoline-3-carboxylic acid;
2-(4-tert-butoxycarbonylamino-benzylamino)-7-methoxy-quinoline-3-carboxylic acid;
2-(4-amino-benzylamino)-7-methoxy-quinoline-3-carboxylic acid;
7-methoxy-2-(2,4,6-trimethoxy-benzylamino)-quinoline-3-carboxylic acid;
7-methoxy-2-[3-(3-phenyl-ureido)-benzylamino]-quinoline-3-carboxylic acid;

7-methoxy-2-[4-(3-phenyl-ureido)-benzylamino]-quinoline-3-carboxylic acid;
7-methoxy-2-[4-(toluene-4-sulfonylamino)-benzylamino]-quinoline-3-carboxylic acid;
7-methoxy-2-(3-ureido-benzylamino)-quinoline-3-carboxylic acid;
2-(dimethylaminosulfonylamino-benzylamino)-7-methoxy-quinoline-3-carboxylic acid;
7-methoxy-2-[2-(4-methoxy-phenyl)-ethylamino]-quinoline-3-carboxylic acid;
7-methoxy-2-[2-(2-methoxy-phenyl)-ethylamino]-quinoline-3-carboxylic acid;
7-methoxy-2-(4-methoxy-benzylamino)-quinoline-3-carboxylic acid;
2-[(benzo[1,3]dioxol-5-ylmethyl)-amino]-7-methoxy-quinoline-3-carboxylic acid;
7-methoxy-2-(3-trifluoromethyl-benzylamino)-quinoline-3-carboxylic acid;
7-methoxy-2-[2-(4-nitro-phenyl)-ethylamino]-quinoline-3-carboxylic acid;
2-(3-imidazol-1-yl-propylamino)-7-methoxy-quinoline-3-carboxylic acid;
7-methoxy-2-(4-sulfamoyl-benzylamino)-quinoline-3-carboxylic acid;
7-methoxy-2-(3-methoxy-benzylamino)-quinoline-3-carboxylic acid;
2-(2-chloro-benzylamino)-7-methoxy-quinoline-3-carboxylic acid;
2-[2-(3-fluoro-phenyl)-ethylamino]-7-methoxy-quinoline-3-carboxylic acid;
2-[2-(4-amino-phenyl)-ethylamino]-7-methoxy-quinoline-3-carboxylic acid;
2-(3-amino-benzylamino)-7-methoxy-quinoline-3-carboxylic acid;
2-(2-benzo[1,3]dioxol-5-yl-ethylamino)-7-methoxy-quinoline-3-carboxylic acid;
7-methoxy-2-[2-(3-methoxy-phenyl)-ethylamino]-quinoline-3-carboxylic acid;
2-[2-(3-chloro-phenyl)-ethylamino]-7-methoxy-quinoline-3-carboxylic acid;
7-methoxy-2-[2-(4-sulfamoyl-phenyl)-ethylamino]-quinoline-3-carboxylic acid;
2-[2-(2-chloro-phenyl)-ethylamino]-7-methoxy-quinoline-3-carboxylic acid;
2-[2-(4-hydroxy-phenyl)-ethylamino]-7-methoxy-quinoline-3-carboxylic acid;
2-(3-bromo-benzylamino)-7-methoxy-quinoline-3-carboxylic acid;
2-(3-chloro-benzylamino)-7-methoxy-quinoline-3-carboxylic acid;
7-methoxy-2-(2-piperazin-1-yl-ethylamino)-quinoline-3-carboxylic acid;
7-methoxy-2-[2-(1-methyl-pyrrolidin-2-yl)-ethylamino]-quinoline-3-carboxylic acid;
7-methoxy-2-piperidin-1-yl-quinoline-3-carboxylic acid;
2-(4-chloro-benzylamino)-7-methoxy-quinoline-3-carboxylic acid;
2-(4-hydroxy-piperidin-1-yl)-7-methoxy-quinoline-3-carboxylic acid;
2-(tert-butoxycarbonylmethyl-amino)-7-methoxy-quinoline-3-carboxylic acid;
2-[2-(2-hydroxy-ethoxy)-ethylamino]-7-methoxy-quinoline-3-carboxylic acid;
7-methoxy-2-(3-methoxy-propylamino)-quinoline-3-carboxylic acid;
7-methoxy-2-(2-methoxy-ethylamino)-quinoline-3-carboxylic acid;
2-(3-hydroxy-propylamino)-7-methoxy-quinoline-3-carboxylic acid;
2-(2-carboxy-ethylamino)-7-methoxy-quinoline-3-carboxylic acid;
7-methoxy-2-propylamino-quinoline-3-carboxylic acid;
2-(carboxymethyl-amino)-7-methoxy-quinoline-3-carboxylic acid;
3-(2-chloro-phenylamino)-6-methoxy-naphthalene-2-carboxylic acid;
2-(2-chloro-phenylamino)-7-methoxy-quinoline-3-carboxylic acid phenylamide;
2-(2-chloro-phenylamino)-7-hydroxy-quinoline-3-carboxylic acid phenylamide;
2-(2-chloro-phenylamino)-7-hydroxy-quinoline-3-carboxylic acid;
2-(2-chloro-phenylamino)-7-(2-hydroxy-ethoxy)-quinoline-3-carboxylic acid;
2-(3,4-dichlorophenylamino)-7-methoxy-quinoline-3-carboxylic acid;
2-(3-biphenylamino)-7-methoxy-quinoline-3-carboxylic acid;
7-methoxy-2-(phenylamino)-quinoline-3-carboxylic acid;
7-methoxy-2-(methyl-3-methylphenylamino)-quinoline-3-carboxylic acid;
2-(cyclohexylamino)-7-methoxy-quinoline-3-carboxylic acid;
2-(3-chlorophenylamino)-6,7-dimethoxy-quinoline-3-carboxylic acid;
2-(3-chlorophenylamino)-6,7-methylenedioxy-quinoline-3-carboxylic acid;
2-(3-chlorophenylamino)-7-hydroxy-quinoline-3-carboxylic acid;
8-bromo-2-(3-chlorophenylamino)-7-hydroxy-quinoline-3-carboxylic acid;
2-(3-chlorophenylamino)-7-methoxy-quinoline-3-carboxamide phenylsulphonamide;
2-(3-chlorophenylamino)-7-methoxy-quinoline-3-carboxamide-2-nitro-phenylsulphonamide;
2-(3-chlorophenylamino)-7-methoxy-quinoline-3-carboxamide methylsulphonamide;
8-bromo-2-(3-chlorophenylamino)-7-methoxy-quinoline-3-carboxylic acid;
2-(3-acetophenylamino)-7-methoxy-quinoline-3-carboxylic acid;
2-(2-benzophenone-yl-amino)-7-methoxy-quinoline-3-carboxylic acid;
2-(2-fluoro-5-methylphenylamino)-7-methoxy-quinoline-3-carboxylic acid;
2-(2-cyanophenylamino)-7-methoxy-quinoline-3-carboxylic acid;
2-(2-chloro-6-methylphenylamino)-7-methoxy-quinoline-3-carboxylic acid;
2-(4-carboxybenzylamino)-7-methoxy-quinoline-3-carboxylic acid;
2-(3-chloro-6-methoxyphenylamino)-7-methoxy-quinoline-3-carboxylic acid;
2-(2-ethylphenylamino)-7-methoxy-quinoline-3-carboxylic acid;
7-methoxy-2-(4-nitrophenylamino)-quinoline-3-carboxylic acid;
2-(4-carboxamidophenylamino)-7-methoxy-quinoline-3-carboxylic acid;
7-methoxy-2-(4-hydroxyphenethylamino)-quinoline-3-carboxylic acid; and
7-methoxy-2-(piperidin-4-ol)-quinoline-3-carboxylic acid;
or a salt thereof.

2. A compound selected from the group consisting of:
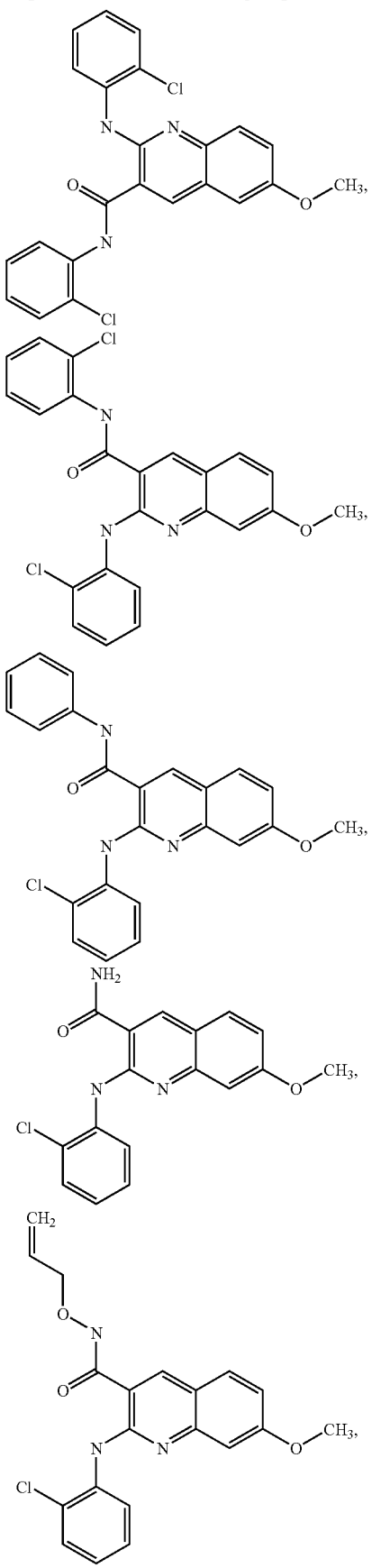
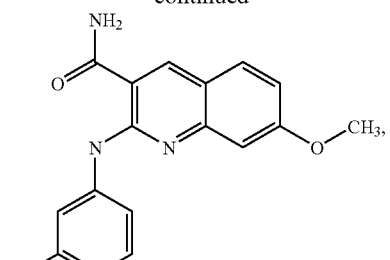
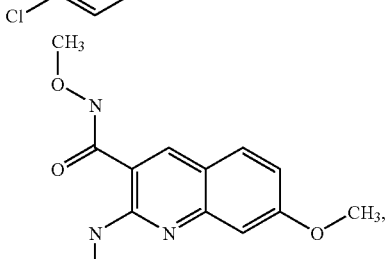
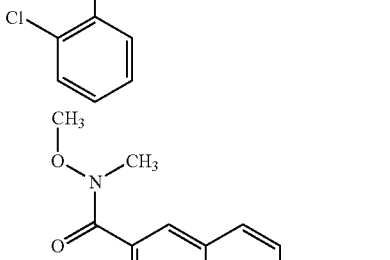
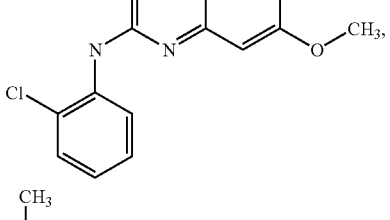
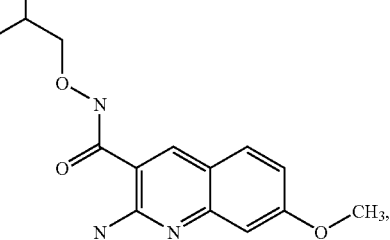
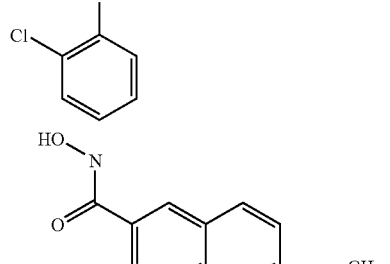, and
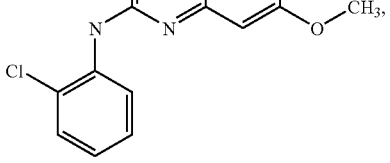
or a salt thereof.

3. A pharmaceutical composition, comprising: a therapeutically effective amount of a compound as claimed in claim 1, or a salt thereof and one or more of pharmaceutically acceptable carriers, diluents and excipients.

4. A pharmaceutical composition, comprising: a therapeutically effective amount of a compound as claimed in claim 2, or a salt thereof and one or more of pharmaceutically acceptable carriers, diluents and excipients.

* * * * *